US008697642B2

(12) United States Patent
Lira et al.

(10) Patent No.: US 8,697,642 B2
(45) Date of Patent: Apr. 15, 2014

(54) DIG-10 INSECTICIDAL CRY TOXINS

(75) Inventors: Justin M. Lira, Fishers, IN (US); Kenneth Narva, Zionsville, IN (US); Aaron T. Woosley, Fishers, IN (US); Ignacio M. Larrinua, Indianapolis, IN (US); Timothy D. Hey, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 638 days.

(21) Appl. No.: 12/814,766

(22) Filed: Jun. 14, 2010

(65) Prior Publication Data

US 2010/0319092 A1 Dec. 16, 2010

Related U.S. Application Data

(60) Provisional application No. 61/187,436, filed on Jun. 16, 2009.

(51) Int. Cl.

*A01N 37/18* (2006.01)

*C12N 15/32* (2006.01)

(52) U.S. Cl.

USPC ........................................ 514/4.5; 536/23.71

(58) Field of Classification Search

None

See application file for complete search history.

(56) References Cited

U.S. PATENT DOCUMENTS 8,314,292 B2 * 11/2012 Carozzi et al. ................ 800/302

FOREIGN PATENT DOCUMENTS

| | | | | |
|---|---|---|---|---|
| WO | WO 2006/119457 A1 * | 9/2006 | | 424/405 |
| WO | WO 2007/035650 * | 3/2007 | | |
| WO | WO 2007/035650 A2 * | 3/2007 | | 800/279 |

OTHER PUBLICATIONS

Tigue et al., "The alpha-helix 4 residue, Asn135, is involved in the oligomerization of Cry1Ac1 and Cry1Ab5 *Bacillus thuringiensis* toxins" Appl Environ Microbiol. 67(12):5715-20 (2001).*

Lu et al., "Identification of Amino Acid Residues of *Bacillus thuringiensis*—Endotoxin CrylAa Associated with Membrane Binding and Toxicity to *Bombyx mori*," J. Bacter. 176(17):5554-59 (1994).*

GenBank Listing CAA23772.1, citing in turn Slighton et al. Cell 21(3):627-38(1980).*

Florez et al., "Protein Engineering of *Bacillus thuringiensis* .delta.-Endotoxins", *Bacillus thuringiensis* Biotechnology, ed: E. Sansinenea, pp. 93-113 (2012).*

* cited by examiner

*Primary Examiner* — David H Kruse

*Assistant Examiner* — Russell Boggs

(74) *Attorney, Agent, or Firm* — Ronald S. Maciak; Faegre Baker Daniels LLP

(57) ABSTRACT

DIG-10 Cry toxins, polynucleotides encoding such toxins, use of such toxins to control pests, and transgenic plants that produce such toxins are disclosed.

3 Claims, No Drawings

SEQUENCE LISTING

```
<160> NUMBER OF SEQ ID NOS: 7

<210> SEQ ID NO 1
<211> LENGTH: 3393
<212> TYPE: DNA
<213> ORGANISM: Bacillus thuringiensis

<400> SEQUENCE: 1
atgaatcaaa aaaactatga aattatagat gcttcaacaa acggtataat tgaattacct      60
gaagattaca atgctatagt cagcccctat aatgctccag catccgttac tacaactatt     120
gaaattactg gaaccatact aagcgattta ggtgttccag gagcatcctc agttagttta     180
cttttgaata aactttaaa tttattatgg ccaaatgata ccaatactgt gtggggaca       240 ttcggaaaag aaaccgctga tcttctaaat gaagtgttat ctccagatga tccagtagta     300
ttaacagcaa atgaatattt agaagggcta aaaataacc ttgatttata tttacaggca     360
cttaaagaat ggaaaaatga tccccaaaat acagcatcca aaggtcgtgt cacagatagg     420
tttcgtattt tggatagtct ttttgaacag tatttgcctt cctttgctag agctggatat     480
gaaactaagc tattaacagt ttatgcacaa gctgcaaatc ttcatatact tttattaaga     540
gatgcttcta tgtttggaga aggttgggga ttgactcaaa caaacataaa tgataactat     600
gatcgccaat tacgattgac agcaaaatac acggaccata gtgtaaagtg gtataacgca     660
ggattagaaa aattaaaagg gaatttaact ggggaaagtt ggtacactta taatagattt     720
cgtagagaaa tgacattaat ggtgttagac gtagtggcat tatttccaaa ctatgataca     780
cgaatgtacc cgatcgcaac atcatcagaa cttacaagaa tgatttatac agatccaatt     840
gcttatacac aaagcgatcc atggtacaag ataacatctc tttcttttc aaatattgaa     900 aatagcgcga ttccaagtcc ttctttcttt aggtggctaa aatccgtttc aattaatagc     960
```

```
cagtggtggg gtagtggtcc tagtcaaacc tactattggg ttggacatga attggtatat    1020
tctaattcaa attctaatca atcacttaag gttaaatatg gagactccaa ttcttatatt    1080
gagcctcctg attctttcag tttttcttct acggatgttt acagaaccat ctctgttgtt    1140
agaaattcag taagtaatta tatagtaagt gaagtccaat tcaattcaat tagtaataca    1200
aatcaaatta gtgaagaaat ttataaacac caatcaaatt ggagtagaaa agaaaccaaa    1260
gattcaatta cagaactatc cttagctgct aatcccccaa catcatttgg aaatgtagca    1320
gaatacagtc atagattagc atatatttca gaggcatacc aaagtcacaa cccatcaaaa    1380
tacccaacct acattcctgt attcggttgg acgcatacaa gcgtacgtta cgataataaa    1440
attttccccg acaaaatcac tcaaattcca gctgttaaaa gctcctcagc ccaaggtgga    1500
tcatggaaaa atatagtgaa aggtcccggg tttactggag gagatgtgac aactgcagtt    1560
tcgccagcaa ctgtaaccga cataataaaa atacaagtta ctctagatcc aaattcactt    1620
tcacaaaaat atcgtgcacg acttcgctat gcttccaatg catttgtacc agctacattg    1680
tatacaaata caagtagtaa ttataatttt gaacttaaaa aaggtacaac tgaacagttt    1740
acaacatata attcatacca gtatgtagat atcccaggtt caatacaatt taataatact    1800
tctgatacag tctctgttta tttgcatatg gattcaacat ctaatgtaaa cgttcatgta    1860
gatagaattg aattcattcc aatagatgaa aattacgatg aaagagttca attgaaaaaa    1920
gcacagaaag ccgtgaatgc cttgtttaca gcgggaaaaa atgcactcca aacagatgta    1980
acagattaca aagtggatca ggtttcaatt ttagtggatt gtgtaacagg ggagttatat    2040
ccaaatgaga aacgcgaact attaagttta gttaaatatg caaaacgttt aagctattcg    2100
cggaatttac ttctggatcc aacattcgac tctatcaatt cgtctgagga gaatggctgg    2160
tacggaagta atggtatcgc aattggcagt gggaatattg tattcaaagg aaactattta    2220
attttctcag gtaccaatga tgaacagtat ccaacgtatc tctatcaaaa aatagacgaa    2280
tctaagttaa aagaatatac acgttataaa ctgagaggtt ttatcgagag tagtcaggat    2340
ttagaagcat acgtgattcg ttatgatgca aaacatcaaa caatggatgt atccaataat    2400
ctattctcag atattactcc tgtaaatgca tgcggagaac caaatcgttg tgcggcacta    2460
ccatacctgg atgaaaatcc aagattagca tgtagttcga tacaagatgg tattttatct    2520
gattcgcatt cgttttctct ccatatagat acaggttcaa ttgatttcaa tgagaacgta    2580
ggaatttggg tggtgtttaa aatttccaca ccggaagggt atgcgaaatt tggaaaccta    2640
gaagtgattg aagatggccc agtcattgga gaagcattag cccgtgtgaa acgccaagaa    2700
atgaagtgga gaaacaagtt ggcacaattg agaacggaaa cacaagcgat ttatacacga    2760
gcaaaacaag ccattgataa tttattcaca aatgcacagg actctcactt aaaaataggt    2820
gcgacatttg cgtcaattgt ggctgcacga agattgtcc aatccatacg tgaagcgtat    2880
atgtcatggt tatctattgt cccaggtata aattatccta tatttacaga attgaatgag    2940
agaatacagc aagcatttca attatatgat gtacgaaatg tcgtacgtaa tggccgattc    3000
cagagtggaa catccgattg gattgtaacc tctgacgtaa gggtacaaga agaaaatggg    3060
aataacgtat tagttctttc caattgggat gcgcaagtat tacaatgcat gacgctctat    3120
caagaccgtg gtatatcttt acgcgtaaca gcacgtaaag aaggactggg cgaagggtat    3180
gtaacaatca ctgatgaaga aggaaatacg gatcaattga gatttggtgg atgcgaggag    3240
atagatgcat ctaactcgtt cgtatccaca ggttatatga caaagaact agaatttttc    3300 ccagatacag agaaagtgcg tatagaaatt ggagaaacag aaggaacatt ccaggtggaa    3360
```
agtgttgaat tattcttgat ggaagatcta tgt    3393

<210> SEQ ID NO 2
<211> LENGTH: 1131
<212> TYPE: PRT
<213> ORGANISM: Bacillus thuringiensis

<400> SEQUENCE: 2

Met Asn Gln Lys Asn Tyr Glu Ile Ile Asp Ala Ser Thr Asn Gly Ile
1               5                   10                  15

Ile Glu Leu Pro Glu Asp Tyr Asn Ala Ile Val Ser Pro Tyr Asn Ala
            20                  25                  30

Pro Ala Ser Val Thr Thr Thr Ile Glu Ile Thr Gly Thr Ile Leu Ser
        35                  40                  45

Asp Leu Gly Val Pro Gly Ala Ser Ser Val Ser Leu Leu Leu Asn Lys
    50                  55                  60

Leu Leu Asn Leu Leu Trp Pro Asn Asp Thr Asn Thr Val Trp Gly Thr
65                  70                  75                  80

Phe Gly Lys Glu Thr Ala Asp Leu Leu Asn Glu Val Leu Ser Pro Asp
                85                  90                  95

Asp Pro Val Val Leu Thr Ala Asn Glu Tyr Leu Glu Gly Leu Lys Asn
            100                 105                 110

Asn Leu Asp Leu Tyr Leu Gln Ala Leu Lys Glu Trp Lys Asn Asp Pro
        115                 120                 125

Gln Asn Thr Ala Ser Lys Gly Arg Val Thr Asp Arg Phe Arg Ile Leu
    130                 135                 140

Asp Ser Leu Phe Glu Gln Tyr Leu Pro Ser Phe Ala Arg Ala Gly Tyr
145                 150                 155                 160

Glu Thr Lys Leu Leu Thr Val Tyr Ala Gln Ala Ala Asn Leu His Ile
                165                 170                 175

Leu Leu Leu Arg Asp Ala Ser Met Phe Gly Glu Gly Trp Gly Leu Thr
            180                 185                 190

Gln Thr Asn Ile Asn Asp Asn Tyr Asp Arg Gln Leu Arg Leu Thr Ala
        195                 200                 205

Lys Tyr Thr Asp His Ser Val Lys Trp Tyr Asn Ala Gly Leu Glu Lys
    210                 215                 220

Leu Lys Gly Asn Leu Thr Gly Glu Ser Trp Tyr Thr Tyr Asn Arg Phe
225                 230                 235                 240

Arg Arg Glu Met Thr Leu Met Val Leu Asp Val Val Ala Leu Phe Pro
                245                 250                 255

Asn Tyr Asp Thr Arg Met Tyr Pro Ile Ala Thr Ser Ser Glu Leu Thr
            260                 265                 270

Arg Met Ile Tyr Thr Asp Pro Ile Ala Tyr Thr Gln Ser Asp Pro Trp
        275                 280                 285

Tyr Lys Ile Thr Ser Leu Ser Phe Ser Asn Ile Glu Asn Ser Ala Ile
    290                 295                 300

Pro Ser Pro Ser Phe Phe Arg Trp Leu Lys Ser Val Ser Ile Asn Ser
305                 310                 315                 320

Gln Trp Trp Gly Ser Gly Pro Ser Gln Thr Tyr Tyr Trp Val Gly His
                325                 330                 335

Glu Leu Val Tyr Ser Asn Ser Asn Ser Asn Gln Ser Leu Lys Val Lys
            340                 345                 350

Tyr Gly Asp Ser Asn Ser Tyr Ile Glu Pro Pro Asp Ser Phe Ser Phe
        355                 360                 365

Ser Ser Thr Asp Val Tyr Arg Thr Ile Ser Val Val Arg Asn Ser Val

```
                370                 375                 380
Ser Asn Tyr Ile Val Ser Glu Val Gln Phe Asn Ser Ile Ser Asn Thr
385                 390                 395                 400

Asn Gln Ile Ser Glu Glu Ile Tyr Lys His Gln Ser Asn Trp Ser Arg
                405                 410                 415

Lys Glu Thr Lys Asp Ser Ile Thr Glu Leu Ser Leu Ala Ala Asn Pro
                420                 425                 430

Pro Thr Ser Phe Gly Asn Val Ala Glu Tyr Ser His Arg Leu Ala Tyr
                435                 440                 445

Ile Ser Glu Ala Tyr Gln Ser His Asn Pro Ser Lys Tyr Pro Thr Tyr
450                 455                 460

Ile Pro Val Phe Gly Trp Thr His Thr Ser Val Arg Tyr Asp Asn Lys
465                 470                 475                 480

Ile Phe Pro Asp Lys Ile Thr Gln Ile Pro Ala Val Lys Ser Ser Ser
                485                 490                 495

Ala Gln Gly Gly Ser Trp Lys Asn Ile Val Lys Gly Pro Gly Phe Thr
                500                 505                 510

Gly Gly Asp Val Thr Thr Ala Val Ser Pro Ala Thr Val Thr Asp Ile
                515                 520                 525

Ile Lys Ile Gln Val Thr Leu Asp Pro Asn Ser Leu Ser Gln Lys Tyr
530                 535                 540

Arg Ala Arg Leu Arg Tyr Ala Ser Asn Ala Phe Val Pro Ala Thr Leu
545                 550                 555                 560

Tyr Thr Asn Thr Ser Ser Asn Tyr Asn Phe Glu Leu Lys Lys Gly Thr
                565                 570                 575

Thr Glu Gln Phe Thr Thr Tyr Asn Ser Tyr Gln Tyr Val Asp Ile Pro
                580                 585                 590

Gly Ser Ile Gln Phe Asn Asn Thr Ser Asp Thr Val Ser Val Tyr Leu
                595                 600                 605

His Met Asp Ser Thr Ser Asn Val Asn Val His Val Asp Arg Ile Glu
                610                 615                 620

Phe Ile Pro Ile Asp Glu Asn Tyr Asp Glu Arg Val Gln Leu Glu Lys
625                 630                 635                 640

Ala Gln Lys Ala Val Asn Ala Leu Phe Thr Ala Gly Lys Asn Ala Leu
                645                 650                 655

Gln Thr Asp Val Thr Asp Tyr Lys Val Asp Gln Val Ser Ile Leu Val
                660                 665                 670

Asp Cys Val Thr Gly Glu Leu Tyr Pro Asn Glu Lys Arg Glu Leu Leu
                675                 680                 685

Ser Leu Val Lys Tyr Ala Lys Arg Leu Ser Tyr Ser Arg Asn Leu Leu
                690                 695                 700

Leu Asp Pro Thr Phe Asp Ser Ile Asn Ser Ser Glu Glu Asn Gly Trp
705                 710                 715                 720

Tyr Gly Ser Asn Gly Ile Ala Ile Gly Ser Gly Asn Ile Val Phe Lys
                725                 730                 735

Gly Asn Tyr Leu Ile Phe Ser Gly Thr Asn Asp Glu Gln Tyr Pro Thr
                740                 745                 750

Tyr Leu Tyr Gln Lys Ile Asp Glu Ser Lys Leu Lys Glu Tyr Thr Arg
                755                 760                 765

Tyr Lys Leu Arg Gly Phe Ile Glu Ser Ser Gln Asp Leu Glu Ala Tyr
                770                 775                 780

Val Ile Arg Tyr Asp Ala Lys His Gln Thr Met Asp Val Ser Asn Asn
785                 790                 795                 800
```

```
Leu Phe Ser Asp Ile Thr Pro Val Asn Ala Cys Gly Glu Pro Asn Arg
            805                 810                 815

Cys Ala Ala Leu Pro Tyr Leu Asp Glu Asn Pro Arg Leu Ala Cys Ser
        820                 825                 830

Ser Ile Gln Asp Gly Ile Leu Ser Asp Ser His Ser Phe Ser Leu His
        835                 840                 845

Ile Asp Thr Gly Ser Ile Asp Phe Asn Glu Asn Val Gly Ile Trp Val
    850                 855                 860

Val Phe Lys Ile Ser Thr Pro Glu Gly Tyr Ala Lys Phe Gly Asn Leu
865                 870                 875                 880

Glu Val Ile Glu Asp Gly Pro Val Ile Gly Ala Leu Ala Arg Val
                885                 890                 895

Lys Arg Gln Glu Met Lys Trp Arg Asn Lys Leu Ala Gln Leu Arg Thr
                900                 905                 910

Glu Thr Gln Ala Ile Tyr Thr Arg Ala Lys Gln Ala Ile Asp Asn Leu
            915                 920                 925

Phe Thr Asn Ala Gln Asp Ser His Leu Lys Ile Gly Ala Thr Phe Ala
    930                 935                 940

Ser Ile Val Ala Ala Arg Lys Ile Val Gln Ser Ile Arg Glu Ala Tyr
945                 950                 955                 960

Met Ser Trp Leu Ser Ile Val Pro Gly Ile Asn Tyr Pro Ile Phe Thr
                965                 970                 975

Glu Leu Asn Glu Arg Ile Gln Gln Ala Phe Gln Leu Tyr Asp Val Arg
            980                 985                 990

Asn Val Val Arg Asn Gly Arg Phe Gln Ser Gly Thr Ser Asp Trp Ile
                995                1000                1005

Val Thr Ser Asp Val Arg Val Gln Glu Glu Asn Gly Asn Asn Val
   1010                1015                1020

Leu Val Leu Ser Asn Trp Asp Ala Gln Val Leu Gln Cys Met Thr
   1025                1030                1035

Leu Tyr Gln Asp Arg Gly Tyr Ile Leu Arg Val Thr Ala Arg Lys
   1040                1045                1050

Glu Gly Leu Gly Glu Gly Tyr Val Thr Ile Thr Asp Glu Glu Gly
   1055                1060                1065

Asn Thr Asp Gln Leu Arg Phe Gly Gly Cys Glu Glu Ile Asp Ala
   1070                1075                1080

Ser Asn Ser Phe Val Ser Thr Gly Tyr Met Thr Lys Glu Leu Glu
   1085                1090                1095

Phe Phe Pro Asp Thr Glu Lys Val Arg Ile Glu Ile Gly Glu Thr
   1100                1105                1110

Glu Gly Thr Phe Gln Val Glu Ser Val Glu Leu Phe Leu Met Glu
   1115                1120                1125

Asp Leu Cys
   1130

<210> SEQ ID NO 3
<211> LENGTH: 1893
<212> TYPE: DNA
<213> ORGANISM: Artificial Sequence
<220> FEATURE:
<223> OTHER INFORMATION: Synthetic Molecule

<400> SEQUENCE: 3
atgaaccaga agaactacga gatcatagac gcttcgacaa atggaatcat tgaactgcca     60
gaggactaca atgccattgt gtctccttac aatgctccag cgagcgtcac cacgacaatc    120
```

```
gaaatcactg gcaccattct cagcgatctc ggtgttcctg gtgcaagcag cgtctctctg    180
ctgctcaaca agctgctgaa tctgctgtgg cctaatgata caaacactgt ctggggaact    240
ttcggcaaag aaactgccga tcttctgaac gaggttttgt cgccagatga tccggtggtc    300
ctcaccgcaa acgagtatct cgaaggactc aagaacaatc tggatcttta cttgcaagcg    360
cttaaggaat ggaagaatga tccccagaac acagcgtcca agggacgggt gacggatcgc    420
tttaggattc ttgactctct cttcgagcag tatctgccat ccttcgcaag agctggctac    480
gaaactaaac tcctcactgt ctatgcccaa gctgctaatc tccacattct gctcttgaga    540
gacgcctcaa tgtttgggga gggctggggt ctgacccaga ccaacatcaa tgacaactac    600
gacagacagc tgaggctgac agccaagtac acggaccact ccgttaagtg gtacaatgct    660
gggcttgaga agctcaaggg gaacctcacc ggagagtctt ggtacaccta caaccgcttc    720
agacgggaga tgacccttat ggttttggac gtcgttgcac tgtttccaaa ctacgacact    780
cgcatgtatc ctattgcgac ctcaagcgaa ctcactcgga tgatctatac tgacccaata    840
gcctacactc agtctgatcc gtggtacaag atcacgtcgt tgtccttctc caacattgag    900
aactcagcca ttccgtctcc ctccttcttt cgctggttga agtcggtttc gatcaacagc    960
caatggtggg gttcgggacc ctcgcagacg tactactggg tcggtcacga actcgtctac   1020
tcgaactcaa actccaatca gagcttgaaa gtgaagtatg gggacagcaa ttcttacatt   1080
gagcctccgg actccttctc attctcgtcc acagacgtgt ataggaccat ctcagtcgtg   1140
aggaactcag tgtccaacta catagtgtct gaagtccagt tcaattcaat ctccaacacc   1200
aaccagattt ctgaggaaat ctacaagcac agagcaact ggtctcgcaa ggagaccaaa   1260
```
(Note: line 1260 may read "agagcaact" — original: `agagcaact ggtctcgcaa ggagaccaaa`)

```
gattccataa cagagctgtc ccttgcagcg aatcctccca cctcatttgg caatgtggct   1320
gagtactccc ataggctcgc ctacatcagc gaagcctatc aaagccacaa cccgtcaaag   1380
tatcccactt acattccggt ctttggctgg acgcacacat ctgttagata cgacaacaaa   1440
atcttcccag acaagatcac ccagattcca gcggtgaaat cctccagcgc tcaaggaggg   1500
agctggaaga acatcgtcaa aggtcctggc ttcacgggag cgacgtgac gaccgctgtt    1560
```
(Note: "cgacgtgac" may be "cgacgtgac" — original: `gcgacgtgac gaccgctgtt`)

```
tcaccagcca cagtcacaga tatcatcaag atccaagtta cgcttgaccc taacagcttg   1620
agccagaagt atagagcacg gctgcgctac gcgtcaaatg ccttcgtccc agccacgttg   1680
tacaccaaca cgtcctccaa ctacaacttc gagcttaaga agggcacaac ggagcaattc   1740
accacctaca actcttatca atacgtggac ataccctggca gcatccagtt caacaacacc   1800
tcggacactg tgagcgtgta tcttcacatg gacagcacct ccaatgtgaa cgttcatgtg   1860
gataggatcg agttcattcc catcgacgag aac                                 1893
```

<210> SEQ ID NO 4
<211> LENGTH: 545
<212> TYPE: PRT
<213> ORGANISM: Bacillus thuringiensis

<400> SEQUENCE: 4

```
Leu Glu Ala Glu Ser Asp Leu Glu Arg Ala Gln Lys Ala Val Asn Ala
 1               5                  10                  15

Leu Phe Thr Ser Ser Asn Gln Ile Gly Leu Lys Thr Asp Val Thr Asp
                20                  25                  30

Tyr His Ile Asp Arg Val Ser Asn Leu Val Glu Cys Leu Ser Asp Glu
            35                  40                  45

Phe Cys Leu Asp Glu Lys Lys Glu Leu Ser Glu Lys Val Lys His Ala
        50                  55                  60
```

```
Lys Arg Leu Ser Asp Glu Arg Asn Leu Leu Gln Asp Pro Asn Phe Arg
 65                  70                  75                  80

Gly Ile Asn Arg Gln Leu Asp Arg Gly Trp Arg Gly Ser Thr Asp Ile
             85                  90                  95

Thr Ile Gln Gly Gly Asp Asp Val Phe Lys Glu Asn Tyr Val Thr Leu
            100                 105                 110

Leu Gly Thr Phe Asp Glu Cys Tyr Pro Thr Tyr Leu Tyr Gln Lys Ile
            115                 120                 125

Asp Glu Ser Lys Leu Lys Ala Tyr Thr Arg Tyr Gln Leu Arg Gly Tyr
            130                 135                 140

Ile Glu Asp Ser Gln Asp Leu Glu Ile Tyr Leu Ile Arg Tyr Asn Ala
145                 150                 155                 160

Lys His Glu Thr Val Asn Val Pro Gly Thr Gly Ser Leu Trp Pro Leu
                165                 170                 175

Ser Ala Pro Ser Pro Ile Gly Lys Cys Ala His His Ser His His Phe
            180                 185                 190

Ser Leu Asp Ile Asp Val Gly Cys Thr Asp Leu Asn Glu Asp Leu Gly
            195                 200                 205

Val Trp Val Ile Phe Lys Ile Lys Thr Gln Asp Gly His Ala Arg Leu
210                 215                 220

Gly Asn Leu Glu Phe Leu Glu Glu Lys Pro Leu Val Gly Glu Ala Leu
225                 230                 235                 240

Ala Arg Val Lys Arg Ala Glu Lys Lys Trp Arg Asp Lys Arg Glu Lys
                245                 250                 255

Leu Glu Trp Glu Thr Asn Ile Val Tyr Lys Glu Ala Lys Glu Ser Val
                260                 265                 270

Asp Ala Leu Phe Val Asn Ser Gln Tyr Asp Arg Leu Gln Ala Asp Thr
            275                 280                 285

Asn Ile Ala Met Ile His Ala Ala Asp Lys Arg Val His Ser Ile Arg
            290                 295                 300

Glu Ala Tyr Leu Pro Glu Leu Ser Val Ile Pro Gly Val Asn Ala Ala
305                 310                 315                 320

Ile Phe Glu Glu Leu Glu Gly Arg Ile Phe Thr Ala Phe Ser Leu Tyr
                325                 330                 335

Asp Ala Arg Asn Val Ile Lys Asn Gly Asp Phe Asn Asn Gly Leu Ser
            340                 345                 350

Cys Trp Asn Val Lys Gly His Val Asp Val Glu Glu Gln Asn Asn His
            355                 360                 365

Arg Ser Val Leu Val Val Pro Glu Trp Glu Ala Glu Val Ser Gln Glu
            370                 375                 380

Val Arg Val Cys Pro Gly Arg Gly Tyr Ile Leu Arg Val Thr Ala Tyr
385                 390                 395                 400

Lys Glu Gly Tyr Gly Glu Gly Cys Val Thr Ile His Glu Ile Glu Asn
                405                 410                 415

Asn Thr Asp Glu Leu Lys Phe Ser Asn Cys Val Glu Glu Val Tyr
            420                 425                 430

Pro Asn Asn Thr Val Thr Cys Asn Asp Tyr Thr Ala Thr Gln Glu Glu
            435                 440                 445

Tyr Glu Gly Thr Tyr Thr Ser Arg Asn Arg Gly Tyr Asp Gly Ala Tyr
450                 455                 460

Glu Ser Asn Ser Ser Val Pro Ala Asp Tyr Ala Ser Ala Tyr Glu Glu
465                 470                 475                 480

Lys Ala Tyr Thr Asp Gly Arg Arg Asp Asn Pro Cys Glu Ser Asn Arg
                485                 490                 495
```

```
Gly Tyr Gly Asp Tyr Thr Pro Leu Pro Ala Gly Tyr Val Thr Lys Glu
            500                 505                 510
Leu Glu Tyr Phe Pro Glu Thr Asp Lys Val Trp Ile Glu Ile Gly Glu
        515                 520                 525
Thr Glu Gly Thr Phe Ile Val Asp Ser Val Glu Leu Leu Leu Met Glu
    530                 535                 540
Glu
545

<210> SEQ ID NO 5
<211> LENGTH: 1176
<212> TYPE: PRT
<213> ORGANISM: Artificial Sequence
<220> FEATURE:
<223> OTHER INFORMATION: Synthetic Molecule

<400> SEQUENCE: 5

Met Asn Gln Lys Asn Tyr Glu Ile Ile Asp Ala Ser Thr Asn Gly Ile
1               5                   10                  15
Ile Glu Leu Pro Glu Asp Tyr Asn Ala Ile Val Ser Pro Tyr Asn Ala
            20                  25                  30
Pro Ala Ser Val Thr Thr Thr Ile Glu Ile Thr Gly Thr Ile Leu Ser
        35                  40                  45
Asp Leu Gly Val Pro Gly Ala Ser Ser Val Ser Leu Leu Asn Lys
    50                  55                  60
Leu Leu Asn Leu Leu Trp Pro Asn Asp Thr Asn Thr Val Trp Gly Thr
65                  70                  75                  80
Phe Gly Lys Glu Thr Ala Asp Leu Leu Asn Glu Val Leu Ser Pro Asp
                85                  90                  95
Asp Pro Val Val Leu Thr Ala Asn Glu Tyr Leu Glu Gly Leu Lys Asn
            100                 105                 110
Asn Leu Asp Leu Tyr Leu Gln Ala Leu Lys Glu Trp Lys Asn Asp Pro
        115                 120                 125
Gln Asn Thr Ala Ser Lys Gly Arg Val Thr Asp Arg Phe Arg Ile Leu
    130                 135                 140
Asp Ser Leu Phe Glu Gln Tyr Leu Pro Ser Phe Ala Arg Ala Gly Tyr
145                 150                 155                 160
Glu Thr Lys Leu Leu Thr Val Tyr Ala Gln Ala Ala Asn Leu His Ile
                165                 170                 175
Leu Leu Leu Arg Asp Ala Ser Met Phe Gly Glu Gly Trp Gly Leu Thr
            180                 185                 190
Gln Thr Asn Ile Asn Asp Asn Tyr Asp Arg Gln Leu Arg Leu Thr Ala
        195                 200                 205
Lys Tyr Thr Asp His Ser Val Lys Trp Tyr Asn Ala Gly Leu Glu Lys
    210                 215                 220
Leu Lys Gly Asn Leu Thr Gly Glu Ser Trp Tyr Thr Tyr Asn Arg Phe
225                 230                 235                 240
Arg Arg Glu Met Thr Leu Met Val Leu Asp Val Val Ala Leu Phe Pro
                245                 250                 255
Asn Tyr Asp Thr Arg Met Tyr Pro Ile Ala Thr Ser Ser Glu Leu Thr
            260                 265                 270
Arg Met Ile Tyr Thr Asp Pro Ile Ala Tyr Thr Gln Ser Asp Pro Trp
        275                 280                 285
Tyr Lys Ile Thr Ser Leu Ser Phe Ser Asn Ile Glu Asn Ser Ala Ile
    290                 295                 300
```

-continued

```
Pro Ser Pro Ser Phe Phe Arg Trp Leu Lys Ser Val Ser Ile Asn Ser
305                 310                 315                 320

Gln Trp Trp Gly Ser Gly Pro Ser Gln Thr Tyr Tyr Trp Val Gly His
            325                 330                 335

Glu Leu Val Tyr Ser Asn Ser Asn Ser Asn Gln Ser Leu Lys Val Lys
            340                 345                 350

Tyr Gly Asp Ser Asn Ser Tyr Ile Glu Pro Pro Asp Ser Phe Ser Phe
            355                 360                 365

Ser Ser Thr Asp Val Tyr Arg Thr Ile Ser Val Val Arg Asn Ser Val
370                 375                 380

Ser Asn Tyr Ile Val Ser Glu Val Gln Phe Asn Ser Ile Ser Asn Thr
385                 390                 395                 400

Asn Gln Ile Ser Glu Glu Ile Tyr Lys His Gln Ser Asn Trp Ser Arg
                405                 410                 415

Lys Glu Thr Lys Asp Ser Ile Thr Glu Leu Ser Leu Ala Ala Asn Pro
            420                 425                 430

Pro Thr Ser Phe Gly Asn Val Ala Glu Tyr Ser His Arg Leu Ala Tyr
            435                 440                 445

Ile Ser Glu Ala Tyr Gln Ser His Asn Pro Ser Lys Tyr Pro Thr Tyr
450                 455                 460

Ile Pro Val Phe Gly Trp Thr His Thr Ser Val Arg Tyr Asp Asn Lys
465                 470                 475                 480

Ile Phe Pro Asp Lys Ile Thr Gln Ile Pro Ala Val Lys Ser Ser Ser
                485                 490                 495

Ala Gln Gly Gly Ser Trp Lys Asn Ile Val Lys Gly Pro Gly Phe Thr
            500                 505                 510

Gly Gly Asp Val Thr Thr Ala Val Ser Pro Ala Thr Val Thr Asp Ile
            515                 520                 525

Ile Lys Ile Gln Val Thr Leu Asp Pro Asn Ser Leu Ser Gln Lys Tyr
530                 535                 540

Arg Ala Arg Leu Arg Tyr Ala Ser Asn Ala Phe Val Pro Ala Thr Leu
545                 550                 555                 560

Tyr Thr Asn Thr Ser Asn Tyr Asn Phe Glu Leu Lys Lys Gly Thr
                565                 570                 575

Thr Glu Gln Phe Thr Thr Tyr Asn Ser Tyr Gln Tyr Val Asp Ile Pro
            580                 585                 590

Gly Ser Ile Gln Phe Asn Asn Thr Ser Asp Thr Val Ser Val Tyr Leu
            595                 600                 605

His Met Asp Ser Thr Ser Asn Val Asn Val His Val Asp Arg Ile Glu
610                 615                 620

Phe Ile Pro Ile Asp Glu Asn Leu Glu Ala Glu Ser Asp Leu Glu Arg
625                 630                 635                 640

Ala Gln Lys Ala Val Asn Ala Leu Phe Thr Ser Ser Asn Gln Ile Gly
                645                 650                 655

Leu Lys Thr Asp Val Thr Asp Tyr His Ile Asp Arg Val Ser Asn Leu
            660                 665                 670

Val Glu Cys Leu Ser Asp Glu Phe Cys Leu Asp Glu Lys Lys Glu Leu
            675                 680                 685

Ser Glu Lys Val Lys His Ala Lys Arg Leu Ser Asp Glu Arg Asn Leu
690                 695                 700

Leu Gln Asp Pro Asn Phe Arg Gly Ile Asn Arg Gln Leu Asp Arg Gly
705                 710                 715                 720

Trp Arg Gly Ser Thr Asp Ile Thr Ile Gln Gly Gly Asp Asp Val Phe
                725                 730                 735
```

-continued

Lys Glu Asn Tyr Val Thr Leu Leu Gly Thr Phe Asp Glu Cys Tyr Pro
            740                 745                 750

Thr Tyr Leu Tyr Gln Lys Ile Asp Glu Ser Lys Leu Lys Ala Tyr Thr
            755                 760                 765

Arg Tyr Gln Leu Arg Gly Tyr Ile Glu Asp Ser Gln Asp Leu Glu Ile
770                 775                 780

Tyr Leu Ile Arg Tyr Asn Ala Lys His Glu Thr Val Asn Val Pro Gly
785                 790                 795                 800

Thr Gly Ser Leu Trp Pro Leu Ser Ala Pro Ser Pro Ile Gly Lys Cys
                805                 810                 815

Ala His His Ser His His Phe Ser Leu Asp Ile Asp Val Gly Cys Thr
                820                 825                 830

Asp Leu Asn Glu Asp Leu Gly Val Trp Val Ile Phe Lys Ile Lys Thr
                835                 840                 845

Gln Asp Gly His Ala Arg Leu Gly Asn Leu Glu Phe Leu Glu Glu Lys
850                 855                 860

Pro Leu Val Gly Glu Ala Leu Ala Arg Val Lys Arg Ala Glu Lys Lys
865                 870                 875                 880

Trp Arg Asp Lys Arg Glu Lys Leu Glu Trp Glu Thr Asn Ile Val Tyr
                885                 890                 895

Lys Glu Ala Lys Glu Ser Val Asp Ala Leu Phe Val Asn Ser Gln Tyr
            900                 905                 910

Asp Arg Leu Gln Ala Asp Thr Asn Ile Ala Met Ile His Ala Ala Asp
            915                 920                 925

Lys Arg Val His Ser Ile Arg Glu Ala Tyr Leu Pro Glu Leu Ser Val
930                 935                 940

Ile Pro Gly Val Asn Ala Ala Ile Phe Glu Glu Leu Glu Gly Arg Ile
945                 950                 955                 960

Phe Thr Ala Phe Ser Leu Tyr Asp Ala Arg Asn Val Ile Lys Asn Gly
                965                 970                 975

Asp Phe Asn Asn Gly Leu Ser Cys Trp Asn Val Lys Gly His Val Asp
                980                 985                 990

Val Glu Glu Gln Asn Asn His Arg Ser Val Leu Val Val Pro Glu Trp
            995                 1000                1005

Glu Ala Glu Val Ser Gln Glu Val Arg Val Cys Pro Gly Arg Gly
    1010                1015                1020

Tyr Ile Leu Arg Val Thr Ala Tyr Lys Glu Gly Tyr Gly Glu Gly
    1025                1030                1035

Cys Val Thr Ile His Glu Ile Glu Asn Asn Thr Asp Glu Leu Lys
    1040                1045                1050

Phe Ser Asn Cys Val Glu Glu Val Tyr Pro Asn Asn Thr Val
    1055                1060                1065

Thr Cys Asn Asp Tyr Thr Ala Thr Gln Glu Glu Tyr Glu Gly Thr
    1070                1075                1080

Tyr Thr Ser Arg Asn Arg Gly Tyr Asp Gly Ala Tyr Glu Ser Asn
    1085                1090                1095

Ser Ser Val Pro Ala Asp Tyr Ala Ser Ala Tyr Glu Glu Lys Ala
    1100                1105                1110

Tyr Thr Asp Gly Arg Arg Asp Asn Pro Cys Glu Ser Asn Arg Gly
    1115                1120                1125

Tyr Gly Asp Tyr Thr Pro Leu Pro Ala Gly Tyr Val Thr Lys Glu
    1130                1135                1140

Leu Glu Tyr Phe Pro Glu Thr Asp Lys Val Trp Ile Glu Ile Gly

```
                1145                1150                1155

Glu Thr Glu Gly Thr Phe Ile Val Asp Ser Val Glu Leu Leu Leu
    1160                1165                1170

Met Glu Glu
    1175

<210> SEQ ID NO 6
<211> LENGTH: 1635
<212> TYPE: DNA
<213> ORGANISM: Artificial Sequence
<220> FEATURE:
<223> OTHER INFORMATION: Synthetic Molecule

<400> SEQUENCE: 6
ctcgaggctg aatctgatct cgaaagggca cagaaagctg taaacgcatt gtttacaagt      60
tctaatcaaa tcggactcaa aaccgatgtt acggactatc acatagatag ggtttctaat     120
cttgtggaat gtctttcaga tgagttttgt ttagatgaga agaaagaact ttcagaaaag     180
gtcaagcacg ccaaaagact gtccgatgaa aggaatctcc ttcaagaccc aaactttcgt     240
ggaatcaata gcagctcga cagaggttgg agagggagca cagatatcac cattcaagga     300
ggagatgacg ttttcaaaga gaactatgtc accttgttag cacctttga tgagtgctat     360
ccaacttatc tgtatcagaa gattgatgaa tccaagctga aggcttacac aagatatcag     420
ctcagaggat acatcgagga ctcccaagat ttggagatat acttgattcg ttacaatgca     480
aaacatgaga ccgtgaatgt tcctggtact ggaagtctct ggccactgtc tgctccgtca     540
cctattggga atgtgccca tcactcccac catttctcat ggacataga cgttggctgc     600
acagatttga tgaagatttt gggtgtttgg gtcatcttca agatcaaaac tcaagacgga     660
cacgctcgtt taggaaactt agagtttctt gaagagaagc ccttggttgg ggaggcactt     720
gccagagtaa agagagctga aaagaagtgg agagataaga gggagaaact tgagtgggag     780
actaacattg tgtacaagga agccaaagaa agcgtggatg ctcttttcgt gaactctcag     840
tatgataggt acaagcaga caccaacata gcaatgatac atgcagctga caaaagagtc     900
cattctattc gtgaggctta cttgccagaa cttagtgtga ttcccggtgt caacgctgcc     960
atttttcgagg aattggaagg aagaatcttt acggctttca gcctctatga cgctaggaat    1020
gttatcaaga atggtgattt caacaatggc ctctcatgtt ggaatgtgaa aggtcatgtt    1080
gatgtagagg agcaaaacaa tcaccgtagc gtgctggttg tcccagaatg ggaagccgaa    1140
gtaagccaag aagttagagt ttgccctgga agaggctaca ttctgcgtgt caccgcttac    1200
aaagaaggat atggcgaagg gtgcgtgact attcatgaga ttgagaacaa tactgacgaa    1260
cttaagtttt caaactgcgt cgaggaggaa gtgtatccta caacacagt gacttgtaat    1320
gactatacag caacgcaaga ggaatacgag gggacataca ccagtcgtaa tcgtggttat    1380
gatggtgctt atgaaagcaa ttcatccgtt ccagctgact atgccagtgc ctacgaagag    1440
aaggcttaca cggatggcag aagagataac ccatgtgagt ccaacagagg ttatggtgat    1500
tacactcctc ttccagctgg ttacgtgact aaagagttag agtactttcc ggagactgat    1560
aaggtttgga ttgaaatcgg agagacagaa gggacattca tagtagattc agttgagctt    1620
cttctcatgg aagaa                                                      1635

<210> SEQ ID NO 7
<211> LENGTH: 1635
<212> TYPE: DNA
<213> ORGANISM: Artificial Sequence
<220> FEATURE:
```

<223> OTHER INFORMATION: Synthetic Molecule

<400> SEQUENCE: 7

```
ctcgaggctg aatcggatct tgaaagggca cagaaggcag tcaacgctct cttcaccagc      60
tcaaatcaga ttggccttaa gaccgatgtt actgactatc atatcgacag agtttctaac     120
cttgtcgagt gcctctccga cgagttctgt ctcgacgaaa agaaggaact ctccgagaaa     180
gtgaagcacg cgaaacgcct ctcggatgaa cggaacttgc tgcaagatcc gaacttcaga     240
ggcatcaatc gccagttgga tagaggctgg aggggatcaa ccgacataac cattcaaggt     300
ggggatgatg tgttcaagga aaactacgtg acattgctgg gcaccttcga cgagtgctat     360
cccacgtatc tctatcagaa gattgacgag tccaagctca aagcctacac acgctatcag     420
ctcagaggct acattgagga ctctcaagac ctcgaaatct acttgatcag atacaacgcc     480
aagcacgaga cggtgaacgt ccctgggact gggtcactgt ggccactgtc ggcaccctcg     540
ccaatcggaa agtgcgctca ccacagccac cacttctccc ttgacataga tgttgggtgt     600
acggacttga atgaggatct gggtgtgtgg gtgatcttta agatcaagac ccaagatggt     660
catgcgaggc ttggcaacct tgagttcctt gaagagaagc ctttggtcgg agaggcactg     720
gctcgcgtga agagggctga agaaaatggg agggacaaga gggagaaact ggagtgggag     780
accaacatag tgtacaagga ggccaaggag tcagtggacg cactgtttgt caattcccag     840
tatgataggc tccaagcgga cacgaacatc gccatgatcc atgcagcgga caagagggtt     900
cactccataa gggaggccta tcttccggag ctgtcagtga ttcctggggt caacgcagcc     960
atctttgagg aattggaagg gaggatcttc accgctttct ctctgtacga cgctcggaac    1020
gtcatcaaga atggtgattt caacaatgga ctcagctgct ggaacgtgaa agggcatgtc    1080
gatgttgaag aacagaacaa tcaccgcagc gtgctggtgg ttccggagtg ggaagccgag    1140
gtctcacaag aagtcagagt gtgccctggg aggggttaca tcttgcgggt cacagcctac    1200
aaggaaggtt atggcgaagg ctgtgtcacg atccatgaga tcgaaaacaa cacagacgag    1260
ctgaagtttt ccaactgtgt tgaggaggag gtctatccta acaatactgt tacgtgcaac    1320
gactacacag ccactcaaga ggagtacgag ggcacttaca cctctcgcaa cagaggctac    1380
gacggtgcct acgagtcaaa cagctccgtg ccagcggact acgcctcggc ttacgaagag    1440
aaggcgtaca ccgacggtcg gagggataac ccgtgcgaga gcaatagagg ctatggcgac    1500
tacactcctc tcccagctgg ctacgtgacc aaggagttgg agtactttcc ggagacagac    1560
aaagtctgga ttgagattgg agagacagaa ggcacgttca tcgtggactc tgttgaactc    1620
ttgctgatgg aggag                                                     1635
```

DIG-10 INSECTICIDAL CRY TOXINS

CROSS-REFERENCE TO RELATED APPLICATIONS

This application Claims the benefit of U.S. Provisional Application 61/187,436, filed on Jun. 16, 2009, which is expressly incorporated by reference herein.

FIELD OF THE INVENTION

This invention concerns new insecticidal Cry toxins and their use to control insects.

BACKGROUND OF THE INVENTION

*Bacillus thuringiensis* (B. t.) is a soil-borne bacterium that produces pesticidal crystal proteins known as delta endotoxins or Cry proteins. Cry proteins are oral intoxicants that function by acting on midgut cells of susceptible insects. Some Cry toxins have been shown to have activity against nematodes. An extensive list of delta endotoxins is maintained and regularly updated at the website lifesci.sussex.ac.uk/home/Neil_Crickmore/Bt/intro.html.

Western corn rootworm (WCR), *Diabrotica virgifera virgifera* LeConte, is an economically important corn pest that causes an estimated $1 billion revenue loss each year in North America due to crop yield loss and expenditures for insect management (Metcalf 1986). WCR management practices include crop rotation with soybeans, chemical insecticides and, more recently, transgenic crops expressing B.t. Cry proteins. However, to date only a few examples of B.t. Cry proteins provide commercial levels of efficacy against WCR, including Cry34Ab1/Cry35Ab1 (Ellis et al., 2002), modified Cry3Aa1 (Walters et al., 2008) and modified Cry3Bb1 (Vaughn et al., 2005). These B.t. proteins are highly effective at preventing WCR corn root damage when produced in the roots of transgenic corn (Moellenbeck et al., 2001, Vaughn et al., 2005, U.S. Pat. No. 7,361,813).

Despite the success of WCR-resistant transgenic corn, several factors create the need to discover and develop new Cry proteins to control WCR. First, although production of the currently-deployed Cry proteins in transgenic corn plants provides robust protection against WCR root damage, thereby protecting grain yield, some WCR adults emerge in artificial infestation trials, indicating less than complete larval insect control. Second, development of resistant insect populations threatens the long-term durability of Cry proteins in rootworm control. Lepidopteran insects resistant to Cry proteins have developed in the field for *Plutella xylostella* (Tabashnik, 1994), *Trichoplusia ni* (Janmaat and Myers 2003, 2005), and *Helicoverpa zeae* (Tabashnik et al., 2008). Insect resistance to B.t. Cry proteins can develop through several mechanisms (Heckel et al., (2007), Pigott and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease. Resistance to Cry toxins in species of Lepidoptera has a complex genetic basis, with at least four distinct, major resistance genes. Similarly, multiple genes are predicted to control resistance to Cry toxins in species of Coleoptera. Development of new high potency Cry proteins will provide additional tools for WCR management. Cry proteins with different modes of action can be produced in combination in transgenic corn to prevent the development WCR insect resistance and protect the long term utility of B.t. technology for rootworm control.

BRIEF SUMMARY OF THE INVENTION

The present invention provides insecticidal Cry toxins, including the toxin designated herein as DIG-10 as well as variants of DIG-10, nucleic acids encoding these toxins, methods of controlling pests using the toxins, methods of producing the toxins in transgenic host cells, and transgenic plants that express the toxins. The predicted amino acid sequence of the wild type DIG-10 toxin is given in SEQ ID NO:2.

As described in Example 1, a nucleic acid encoding the DIG-5 protein was isolated from a B.t. strain internally designated by Dow AgroSciences LLC as PS198Q7. The nucleic acid sequence for the full length coding region was determined, and the full length protein sequence was deduced from the nucleic acid sequence. The DIG-5 toxin has some similarity to Cry7Ba1 (Genbank Accession No. ABB70817.1) and other *B. thuringiensis* Cry7-type proteins (see website at lifesci.sussex.ac.uk/home/Neil_Crickmore/Bt/intro.html).

Insecticidally active variants of the DIG-10 toxin are also described herein, and are referred to collectively as DIG-10 toxins.

DIG-10 toxins can be used alone or in combination with other Cry toxins, such as Cry34Ab1/Cry35Ab1 (DAS-59122-7), Cry3Bb1 (MON88017), Cry3A (MIR604), chimeric Cry1Ab/Cry3Aa (FR8A, WO 2009/121633A1), CryET33 and CryET34, Vip1A, Cry1Ia, CryET84, CryET80, CryET76, CryET71, CryET69, CryET75, CryET39, CryET79, and CryET74 to control development of resistant Coleopteran insect populations.

DIG-10 toxins may also be used in combination with RNAi methodologies for control of other insect pests. For example, DIG-10 can be used in transgenic plants in combination with a dsRNA for suppression of an essential gene in corn rootworm or an essential gene in an insect pest. Such target genes include, for example, vacuolar ATPase, ARF-1, Act42A, CHD3, EF-1α, and TFIIB. An example of a suitable target gene is vacuolar ATPase, as disclosed in WO2007/035650.

In one embodiment the invention provides an isolated DIG-10 toxin polypeptide comprising a core toxin segment selected from the group consisting of
 (a) a polypeptide comprising the amino acid sequence of residues 97 to 631 of SEQ ID NO:2;
 (b) a polypeptide comprising an amino acid sequence having at least 90% sequence identity to the amino acid sequence of residues 97 to 631 of SEQ ID NO:2;
 (c) a polypeptide comprising an amino acid sequence of residues 97 to 631 of SEQ ID NO:2 with up to 20 amino acid substitutions, deletions, or modifications that do not adversely affect expression or activity of the toxin encoded by SEQ ID NO:2;
or an insecticidally active fragment thereof.

In another embodiment the invention provides an isolated DIG-10 toxin polypeptide comprising a DIG-10 core toxin segment selected from the group consisting of
 (a) a polypeptide comprising the amino acid sequence of residues 1 to 631 of SEQ ID NO:2;
 (b) a polypeptide comprising an amino acid sequence having at least 90% sequence identity to the amino acid sequence of residues 1 to 631 of SEQ ID NO:2;
 (c) a polypeptide comprising an amino acid sequence of residues 1 to 631 of SEQ ID NO: 2 with up to 20 amino acid substitutions, deletions, or modifications that do not adversely affect expression or activity of the toxin encoded by SEQ ID NO:2;

or an insecticidally active fragment thereof.

In another embodiment the invention provides an isolated DIG-10 toxin polypeptide comprising a DIG-10 core toxin segment selected from the group consisting of
(a) a polypeptide comprising the amino acid sequence of residues 1 to 1131 of SEQ ID NO:2;
(b) a polypeptide comprising an amino acid sequence having at least 90% sequence identity to the amino acid sequence of residues 1 to 1131 of SEQ ID NO:2;
(c) a polypeptide comprising an amino acid sequence of residues 1 to 1131 of SEQ ID NO:2 with up to 20 amino acid substitutions, deletions, or modifications that do not adversely affect expression or activity of the toxin encoded by SEQ ID NO:2;

or an insecticidally active fragment thereof.

In another embodiment the invention provides an isolated DIG-10 toxin polypeptide comprising a DIG-10 core toxin segment selected from the group consisting of
(a) a polypeptide comprising the amino acid sequence of residues 97 to 1131 of SEQ ID NO:2;
(b) a polypeptide comprising an amino acid sequence having at least 90% sequence identity to the amino acid sequence of residues 97 to 1131 of SEQ ID NO:2;
(c) a polypeptide comprising an amino acid sequence of residues 97 to 1131 of SEQ ID NO:2 with up to 20 amino acid substitutions, deletions, or modifications that do not adversely affect expression or activity of the toxin encoded by SEQ ID NO:2;

or an insecticidally active fragment thereof.

In another embodiment the invention provides a plant comprising a DIG-10 toxin.

In another embodiment the invention provides a method for controlling a pest population comprising contacting said population with a pesticidally effective amount of a DIG-10 toxin In another embodiment the invention provides an isolated nucleic acid that encodes a DIG-10 toxin.

In another embodiment the invention provides a DNA construct comprising a nucleotide sequence that encodes a DIG-10 toxin operably linked to a promoter that is not derived from *Bacillus thuringiensis* and is capable of driving expression in a plant. The invention also provides a transgenic plant that comprises the DNA construct stably incorporated into its genome and a method for protecting a plant from a pest comprising introducing the construct into said plant.

BRIEF DESCRIPTION OF THE SEQUENCES

SEQ ID NO:1 DNA sequence encoding full-length DIG-10 toxin; 3393 nt.
SEQ ID NO:2 Full-length DIG-10 protein sequence; 1131 aa.
SEQ ID NO:3 Maize-optimized DIG-10 core toxin coding region; 1893 nt.
SEQ ID NO:4 Cry1Ab protoxin segment; 545 aa.
SEQ ID NO:5 Chimeric toxin: DIG-10 Core/Cry1Ab protoxin segment; 1176 aa.
SEQ ID NO:6 Dicot-optimized DNA sequence encoding the Cry1Ab protoxin segment; 1635 nt
SEQ ID NO:7 Maize-optimized DNA sequence encoding the Cry1Ab protoxin segment; 1635 nt

DETAILED DESCRIPTION OF THE INVENTION

DIG-10 Toxins, and Insecticidally Active Variants.

In addition to the full length DIG-10 toxin of SEQ ID NO:2, the invention encompasses insecticidally active variants. By the term "variant", applicants intend to include fragments, certain deletion and insertion mutants, and certain fusion proteins. DIG-10 is a classic three-domain Cry toxin. As a preface to describing variants of the DIG-10 toxin that are included in the invention, it will be useful to briefly review the architecture of three-domain Cry toxins in general and of the DIG-10 protein toxin in particular.

A majority of *Bacillus thuringiensis* delta-endotoxin crystal protein molecules are composed of two functional segments. The protease-resistant core toxin is the first segment and corresponds to about the first half of the protein molecule. The full ~130 kDa protoxin molecule is rapidly processed to the resistant core segment by proteases in the insect gut. The segment that is deleted by this processing will be referred to herein as the "protoxin segment." The protoxin segment is believed to participate in toxin crystal formation (Arvidson et al., (1989). The protoxin segment may thus convey a partial insect specificity for the toxin by limiting the accessibility of the core to the insect by reducing the protease processing of the toxin molecule (Haider et al., (1986) or by reducing toxin solubility (Aronson et al., (1991). B.t. toxins, even within a certain class, vary to some extent in length and in the precise location of the transition from the core toxin portion to protoxin portion. The transition from core toxin portion to protoxin portion will typically occur at between about 50% to about 60% of the full length toxin. SEQ ID NO:2 discloses the 1131 amino acid sequence of the full-length DIG-10 polypeptide, of which the N-terminal 631 amino acids comprise the DIG-10 core toxin. The 5'-terminal 1893 nucleotides of SEQ ID NO:1 is the coding region for the core toxin.

Three dimensional crystal structures have been determined for Cry1Aa1, Cry2Aa1, Cry3Aa1, Cry3Bb 1, Cry4Aa, Cry4Ba and Cry8Ea1. These structures for the core toxins are remarkably similar and are comprised of three distinct domains with the features described below (reviewed in de Maagd et al., 2003).

Domain I is a bundle of seven alpha helices where helix five is surrounded by six amphipathic helices. This domain has been implicated in pore formation and shares homology with other pore forming proteins including hemolysins and colicins. Domain I of the DIG-10 protein comprises amino acid residues 36 to 262 of SEQ ID NO:2.

Domain II is formed by three anti-parallel beta sheets packed together in a beta prism. The loops of this domain play important roles in binding insect midgut receptors. In Cry1A proteins, surface exposed loops at the apices of domain II beta sheets are involved in binding to Lepidopteran cadherin receptors. Cry3Aa domain II loops bind a membrane-associated metalloprotease of *Leptinotarsa decemlineata* (Say) (Colorado potato beetle) in a similar fashion (Ochoa-Campuzano et al., 2007). Domain II shares homology with certain carbohydrate-binding proteins including vitelline and jacaline. Domain II of the DIG-10 protein comprises amino acid residues 267 to 476 of SEQ ID NO:2.

Domain III is a beta sandwich of two anti-parallel beta sheets. Structurally this domain is related to carbohydrate-binding domains of proteins such as glucanases, galactose oxidase, sialidase and others. Domain III binds certain classes of receptor proteins and perhaps participates in insertion of an oligomeric toxin pre-pore that interacts with a second class of receptors, examples of which are aminopeptidase and alkaline phosphatase in the case of Cry1A proteins (Honée et al., (1991), Pigott and Ellar, 2007)). Analogous Cry Domain III receptors have yet to be identified in Coleoptera. Conserved B.t. sequence blocks 2 and 3 map near the N-terminus and C-terminus of Domain 2, respectively. Hence, these conserved sequence blocks 2 and 3 are approximate boundary regions between the three functional domains. These regions of conserved DNA and protein homology have been exploited for engineering recombinant B.t. toxins (U.S. Pat. No. 6,090,931, WO 91/01087, WO 95/06730, WO 1998022595). Domain III of the DIG-10 protein comprises amino acid residues 486 to 629 of SEQ ID NO:2.

It has been reported that α-helix 1 of domain I is removed following receptor binding. Aronson et al. (1999) demonstrated that Cry1Ac bound to BBMV was protected from proteinase K cleavage beginning at residue 59, just after α-helix 1; similar results were cited for Cry1Ab. Gomez et al., (2002) found that Cry1Ab oligomers formed upon BBMV receptor binding lacked the α-helix 1 portion of domain I. Also, Soberon et al., (2007) have shown that N-terminal deletion mutants of Cry1Ab and Cry1Ac which lack approximately 60 amino acids encompassing α-helix 1 on the three dimensional Cry structure are capable of assembling monomers of molecular weight about 60 kDa into pre-pores in the absence of cadherin binding. These N-terminal deletion mutants were reported to be active on Cry-resistant insect larvae. Furthermore, Diaz-Mendoza et al., (2007) described Cry1Ab fragments of 43 kDa and 46 kDa that retained activity on Mediterranean corn borer (*Sesamia nonagrioides*). These fragments were demonstrated to include amino acid residues 116 to 423; however the precise amino acid sequences were not elucidated and the mechanism of activity of these proteolytic fragments is unknown. The results of Gomez et al., (2002), Soberon et al., 2007 and Diaz-Mendoza et al., (2007) contrast with those of Hofte et al., (1986), who reported that deletion of 36 amino acids from the N-terminus of Cry1Ab resulted in loss of insecticidal activity.

We have deduced the beginning and end of helices 1, 2A, 2B, and 3, and the location of the spacer regions between them in Domain I of the DIG-10 toxin by comparing the DIG-10 protein sequence with the protein sequence for Cry8Ea1, for which the structure is known. These locations are described in Table 1.

7. The subject invention therefore relates in part to improvements to Cry protein efficacy made by engineering the α-helical components of Domain I for more efficient pore formation. More specifically, the subject invention relates in part to improved DIG-10 proteins designed to have N-terminal deletions in regions with putative secondary structure homology to α-helices 1 and 2 in Domain I of Cry1 proteins.

Deletions to improve the insecticidal properties of the DIG-10 toxins may initiate before the predicted α-helix 2A start, and may terminate after the α-helix 2B end, but preferably do not extend into α-helix 3.

In designing coding sequences for the N-terminal deletion variants, an ATG start codon, encoding methionine, is inserted at the 5' end of the nucleotide sequence designed to express the deletion variant. For sequences designed for use in transgenic plants, it may be of benefit to adhere to the "N-end rule" of Varshaysky (1997). It is taught that some amino acids may contribute to protein instability and degradation in eukaryotic cells when displayed as the N-terminal residue of a protein. For example, data collected from observations in yeast and mammalian cells indicate that the N-terminal destabilizing amino acids are F, L, W, Y, R, K, H, I, N, Q, D, E and possibly P. While the specifics of protein degradation mechanisms may differ somewhat between organisms, the conservation of identity of N-terminal destabilizing amino acids seen above suggests that similar mechanisms may function in plant cells. For instance, Worley et al., (1998) found that in plants, the N-end rule includes basic and aromatic residues. It is a possibility that proteolytic cleavage by plant proteases near the start of α-helix 3 of subject B.t. insecticidal proteins may expose a destabilizing N-terminal amino acid. Such processing may target the cleaved proteins for rapid decay and limit the accumulation of the B.t. insecticidal proteins to levels insufficient for effective insect control. Accordingly, for N-terminal deletion variants that begin with one of the destabilizing amino acids, applicants prefer to add a codon that specifies a G (glycine) amino acid between the translational initiation methionine and the destabilizing amino acid.

Example 2 gives specific examples of amino-terminal deletion variants of DIG-10 in accordance with the invention.

TABLE 1

Amino acid coordinates of projected α-helices of DIG-10 protein.

| | Helix1 | spacer | Helix2A | spacer | Helix2B | spacer | Helix3 | spacer | Helix4 |
|---|---|---|---|---|---|---|---|---|---|
| Residues of SEQ ID NO: 2 | 31-49 | 50-55 | 56-70 | 71-79 | 80-89 | 90-96 | 97-126 | 127-130 | 131-151 |

Amino Terminal Deletion Variants of DIG-10

In one of its aspects the invention provides DIG-10 variants in which all or part of helices 1, 2A, and 2B are deleted to improve insecticidal activity and avoid development of resistance by insects. These modifications are made to provide DIG-10 variants with improved attributes, such as improved target pest spectrum, potency, and insect resistance management. In some embodiments of the subject invention, the subject modifications may affect the efficiency of protoxin activation and pore formation, leading to insect intoxication. More specifically, to provide DIG-10 variants with improved attributes, step-wise deletions are described that remove part of the gene encoding the N-terminus. The deletions remove all of α-helix 1 and all or part of α-helix 2 in Domain I, while maintaining the structural integrity of the α-helices 3 through Chimeric Toxins Chimeric proteins utilizing the core toxin domain of one Cry toxin fused to the protoxin segment of another Cry toxin have previously been reported. DIG-10 variants include toxins comprising an N-terminal toxin core portion of a DIG-10 toxin (which may be full length or have the N-terminal deletions described above) fused to a heterologous protoxin segment at some point past the end of the core toxin portion. The transition to the heterologous protoxin segment can occur at approximately the core toxin/protoxin junction or, in the alternative, a portion of the native protoxin (extending past the core toxin portion) can be retained with the transition to the heterologous protoxin occurring downstream. As an example, a chimeric toxin of the subject invention has the full toxin portion of DIG-10 (amino acids 1-631) and a heterologous protoxin (amino acids 632 to the C-terminus). In a preferred embodiment, the heterologous portion of the protoxin is derived from a Cry1Ab delta-endotoxin, as illustrated in SEQ ID NO:5.

SEQ ID NO:4 discloses the 545 amino acid sequence of a Cry1Ab protoxin segment useful in DIG-10 variants of the invention. Attention is drawn to the last about 100 to 150 amino acids of this protoxin segment, which it is most critical to include in the chimeric toxin of the subject invention.

Protease Sensitivity Variants.

Insect gut proteases typically function in aiding the insect in obtaining needed amino acids from dietary protein. The best understood insect digestive proteases are serine proteases, which appear to be the most common type (Englemann and Geraerts, (1980), particularly in Lepidopteran species. Coleopteran insects have guts that are more neutral to acidic than are Lepidopteran guts. The majority of Coleopteran larvae and adults, for example Colorado potato beetle, have slightly acidic midguts, and cysteine proteases provide the major proteolytic activity (Wolfson and Murdock, (1990). More precisely, Thie and Houseman (1990) identified and characterized the cysteine proteases, cathepsin B-like and cathepsin H-like, and the aspartyl protease, cathepsin D-like, in Colorado potato beetle. Gillikin et al., (1992) characterized the proteolytic activity in the guts of western corn rootworm larvae and found primarily cysteine proteases. U.S. Pat. No. 7,230,167 disclosed that the serine protease, cathepsin G, exists in western corn rootworm. The diversity and different activity levels of the insect gut proteases may influence an insect's sensitivity to a particular B.t. toxin.

In another embodiment of the invention, protease cleavage sites may be engineered at desired locations to affect protein processing within the midgut of susceptible larvae of certain insect pests. These protease cleavage sites may be introduced by methods such as chemical gene synthesis or splice overlap PCR (Horton et al., 1989). Serine protease recognition sequences, for example, can optionally be inserted at specific sites in the Cry protein structure to effect protein processing at desired deletion points within the midgut of susceptible larvae. Serine proteases that can be exploited in such fashion include Lepidopteran midgut serine proteases such as trypsin or trypsin-like enzymes, chymotrypsin, elastase, etc. (Christeller et al., 1992). Further, deletion sites identified empirically by sequencing Cry protein digestion products generated with unfractionated larval midgut protease preparations or by binding to brush border membrane vesicles can be engineered to effect protein activation. Modified Cry proteins generated either by gene deletion or by introduction of protease cleavage sites have improved activity on Lepidopteran pests such as *Ostrinia nubilalis, Diatraea grandiosella, Helicoverpa zea, Agrotis ipsilon, Spodoptera frugiperda, Spodoptera exigua, Diatraea saccharalis, Loxagrotis albicosta*, Coleopteran pests such as western corn rootworm, southern corn root worm, northern corn rootworm (i.e. *Diabrotica* spp.) and other target pests.

Coleopteran serine proteases such as trypsin, chymotrypsin and cathepsin G-like protease, Coleopteran cysteine proteases such as cathepsins (B-like, L-like, O-like, and K-like proteases) (Koiwa et al., (2000) and Bown et al., (2004), Coleopteran metalloproteases such as ADAM10 (Ochoa-Campuzano et al., (2007)), and Coleopteran aspartic acid proteases such as cathepsins D-like and E-like, pepsin, plasmepsin, and chymosin may further be exploited by engineering appropriate recognition sequences at desired processing sites to affect Cry protein processing within the midgut of susceptible larvae of certain insect pests.

A preferred location for the introduction of such protease cleavage sites may be within the "spacer" region between α-helix2B and α-helix 3, for example within amino acids 90 to 96 of the full length DIG-10 protein (SEQ ID NO:2 and Table 1). A second preferred location for the introduction of protease cleavage sites may be within the spacer region between α-helix3 and α-helix4 (Table 1), for example within amino acids 127 to 130 of the full length DIG-10 protein of SEQ ID NO:2. Modified Cry proteins generated either by gene deletion or by introduction of protease cleavage sites have improved activity on insect pests including but not limited to western corn rootworm, southern corn root worn, northern corn rootworm, and the like.

Various technologies exist to enable determination of the sequence of the amino acids which comprise the N-terminal or C-terminal residues of polypeptides. For example, automated Edman degradation methodology can be used in sequential fashion to determine the N-terminal amino acid sequence of up to 30 amino acid residues with 98% accuracy per residue. Further, determination of the sequence of the amino acids comprising the carboxy end of polypeptides is also possible (Bailey et al., (1992); U.S. Pat. No. 6,046,053). Thus, in some embodiments, B.t. Cry proteins which have been activated by means of proteolytic processing, for example, by proteases prepared from the gut of an insect, may be characterized and the N-terminal or C-terminal amino acids of the activated toxin fragment identified. DIG-10 variants produced by introduction or elimination of protease processing sites at appropriate positions in the coding sequence to allow, or eliminate, proteolytic cleavage of a larger variant protein by insect, plant or microorganism proteases are within the scope of the invention. The end result of such manipulation is understood to be the generation of toxin fragment molecules having the same or better activity as the intact (full length) toxin protein.

Domains of the DIG-10 Toxin

The separate domains of the DIG-10 toxin, (and variants that are 90, 95, or 97% identical to such domains) are expected to be useful in forming combinations with domains from other Cry toxins to provide new toxins with increased spectrum of pest toxicity, improved potency, or increased protein stability. Domain I of the DIG-10 protein comprises amino acid residues 36 to 262. Domain II of the DIG-10 protein comprises amino acid residues 267 to 476. Domain III of the DIG-10 protein comprises amino acid residues 486 to 629. Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Domain II is involved in receptor binding, and Domain III binds certain classes of receptor proteins and perhaps participates in insertion of an oligomeric toxin pre-pore. Some Domain III substitutions in other toxins have been shown to produce superior toxicity against *Spodoptera exigua* (de Maagd et al., (1996) and guidance exists on the design of the Cry toxin domain swaps (Knight et al., (2004).

Methods for generating recombinant proteins and testing them for pesticidal activity are well known in the art (see, for example, Naimov et al., (2001), de Maagd et al., (1996), Ge et al., (1991), Schnepf et al., (1990), Rang et al., (1999)). Domain I from Cry1A and Cry3A proteins has been studied for the ability to insert and form pores in membranes. α-helices 4 and 5 of domain I play key roles in membrane insertion and pore formation (Walters et al., 1993, Gazit et al., 1998; Nunez-Valdez et al., 2001), with the other helices proposed to contact the membrane surface like the ribs of an umbrella (Bravo et al., (2007); Gazit et al., (1998)).

DIG-10 Variants Created by Making a Limited Number of Amino Acid Deletions, Substitutions, or Additions.

Amino acid deletions, substitutions, and additions to the amino acid sequence of SEQ ID NO:2 can readily be made in a sequential manner and the effects of such variations on insecticidal activity can be tested by bioassay. Provided the number of changes is limited in number, such testing does not involve unreasonable experimentation. The invention includes insecticidally active variants of the core toxin (amino acids 1-631 of SEQ ID NO:2, or amino acid 97-631 of SEQ ID NO:2) in which up to 10, up to 15, or up to 20 amino acid additions, deletions, or substitutions have been made.

The invention includes DIG-10 variants having a core toxin segment that is 90%, 95% or 97% identical to amino acids 1-631 of SEQ ID NO:2 or amino acids 97-631 of SEQ ID NO:2.

Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 2 provides a listing of examples of amino acids belonging to each class.

TABLE 2

| Class of Amino Acid | Examples of Amino Acids |
|---|---|
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the biological activity of the toxin. Variants include polypeptides that differ in amino acid sequence due to mutagenesis. Variant proteins encompassed by the present invention are biologically active, that is they continue to possess the desired biological activity of the native protein, that is, retaining pesticidal activity.

Variant proteins can also be designed that differ at the sequence level but that retain the same or similar overall essential three-dimensional structure, surface charge distribution, and the like. See e.g. U.S. Pat. No. 7,058,515; Larson et al., (2002); Stemmer (1994a, 1994b, 1995); and Crameri et al., (1996a, 1996b, 1997).

Nucleic Acids

Isolated nucleic acids encoding DIG-10 toxins are one aspect of the present invention. This includes nucleic acids encoding SEQ ID NO:2 and SEQ ID NO:5, and complements thereof, as well as other nucleic acids that encode insecticidal variants of SEQ ID NO:2. By "isolated" applicants mean that the nucleic acid molecules have been removed from their native environment and have been placed in a different environment by the hand of man. Because of the redundancy of the genetic code, a variety of different DNA sequences can encode the amino acid sequences disclosed herein. It is well within the skill of a person trained in the art to create these alternative DNA sequences encoding the same, or essentially the same, toxins.

Gene Synthesis

Genes encoding the improved Cry proteins described herein can be made by a variety of methods well-known in the art. For example, synthetic gene segments and synthetic genes can be made by phosphite tri-ester and phosphoramidite chemistry (Caruthers et al, 1987), and commercial vendors are available to perform gene synthesis on demand. Full-length genes can be assembled in a variety of ways including, for example, by ligation of restriction fragments or polymerase chain reaction assembly of overlapping oligonucleotides (Stewart and Burgin, 2005). Further, terminal gene deletions can be made by PCR amplification using site-specific terminal oligonucleotides.

Nucleic acids encoding DIG-10 toxins can be made for example, by synthetic construction by methods currently practiced by any of several commercial suppliers. (See for example, U.S. Pat. No. 7,482,119 B2). These genes, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for a DIG-10 toxin, a coding sequence can be designed by reverse translating the coding sequence using codons preferred by the intended host, and then refining the sequence using alternative codons to remove sequences that might cause problems and provide periodic stop codons to eliminate long open coding sequences in the non-coding reading frames.

Quantifying Sequence Identity

To determine the percent identity of two amino acid sequences or of two nucleic acid sequences, the sequences are aligned for optimal comparison purposes. The percent identity between the two sequences is a function of the number of identical positions shared by the sequences (i.e. percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is that of Altschul et al. (1990), and Karlin and Altschul (1990), modified as in Karlin and Altschul (1993), and incorporated into the BLASTN and BLASTX programs. BLAST searches may be conveniently used to identify sequences homologous (similar) to a query sequence in nucleic or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST Altschul et al., (1997) can be utilized to obtain gapped alignments for comparison purposes, Alternatively, PSI-Blast can be used to perform an iterated search that detects distant relationships between molecules Altschul et al., (1997). When utilizing BLAST, Gapped BLAST, and PSI-Blast programs, the default parameters of the respective programs can be used. See website at ncbi.nlm.nih.gov.

A non-limiting example of a mathematical algorithm utilized for the comparison of sequences is the ClustalW algorithm (Thompson et al., (1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package (available at website emboss.sourceforge.net/). wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE (see website at emboss.sourceforge.net/). GAP Version 10 may be used to determine sequence identity or similarity using the following parameters: for a nucleotide sequence, % identity and % similarity are found using GAP Weight of 50 and Length Weight of 3, and the nwsgapdna.cmp scoring matrix. For amino acid sequence comparison, % identity or % similarity are determined using GAP weight of 8 and length weight of 2, and the BLOSUM62 scoring program.

wNEEDLE reads two input sequences, finds the optimum alignment (including gaps) along their entire length, and writes their optimal global sequence alignment to file. The algorithm explores all possible alignments and chooses the best, using a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Alignment may also be performed manually by inspection.

Recombinant Hosts

The toxin-encoding genes of the subject invention can be introduced into a wide variety of microbial or plant hosts. Expression of the toxin gene results, directly or indirectly, in the intracellular production and maintenance of the pesticidal protein. With suitable microbial hosts, e.g. *Pseudomonas*, the microbes can be applied to the environment of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g. genera *Pseudomonas, Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc,* and *Alcaligenes*; fungi, particularly yeast, e.g. genera *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus,* and *Azotobacter vinelandii*; and phytosphere yeast species such as *Rhodotorula rubra, R.*

*glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

Methods of Controlling Insect Pests

When an insect comes into contact with an effective amount of toxin delivered via transgenic plant expression, formulated protein compositions(s), sprayable protein composition(s), a bait matrix or other delivery system, the results are typically death of the insect, or the insects do not feed upon the source which makes the toxins available to the insects.

The subject protein toxins can be "applied" or provided to contact the target insects in a variety of ways. For example, transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art.

Transgenic Plants

The subject proteins can be used to protect practically any type of plant from damage by an insect pest. Examples of such plants include maize, sunflower, soybean, cotton, canola, rice, sorghum, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is the transformation of plants with genes encoding the subject insecticidal protein or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. No. 4,945,050 and U.S. Pat. No. 5,141,131). Plants may be transformed using *Agrobacterium* technology, see U.S. Pat. No. 5,177,010, U.S. Pat. No. 5,104,310, European Patent Application No. 0131624B1, European Patent Application No. 120516, European Patent Application No. 159418B1, European Patent Application No. 176112, U.S. Pat. No. 5,149,645, U.S. Pat. No. 5,469,976, U.S. Pat. No. 5,464,763, U.S. Pat. No. 4,940,838, U.S. Pat. No. 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. No. 5,231,019, U.S. Pat. No. 5,463,174, U.S. Pat. No. 4,762,785, U.S. Pat. No. 5,004,863, and U.S. Pat. No. 5,159,135. Other transformation technology includes WHISKERS™ technology, see U.S. Pat. No. 5,302,523 and U.S. Pat. No. 5,464,765. Electroporation technology has also been used to transform plants, see WO 87/06614, U.S. Pat. No. 5,472,869, U.S. Pat. No. 5,384,253, WO 9209696, and WO 9321335. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques within the skill of an artisan.

Genes encoding DIG-10 toxins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13 mp series, pACYC184, etc. Accordingly, the sequence encoding the Cry protein or variants can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in European Patent Application No. 120516; Lee and Gelvin (2008), Fraley et al., (1986), and An et al., (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as bialaphos, kanamycin, G418, bleomycin, or hygromycin, inter alfa. The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic B.t. genes for use in plants are known in the art (Stewart 2007).

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus, and the like may be used. Plant promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the leaves or seeds (e.g., zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO 2007/053482 A2), or phenoxy acids herbicides and aryloxyphenoxypropionates herbicides (see WO 2005107437 A2, A3). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein such as that of the subject invention with one or more additional HT traits such as those mentioned above, plus one or more additional input traits (e.g. other insect resistance conferred by B.t.-derived or other insecticidal proteins, insect resistance conferred by mechanisms such as RNAi and the like, disease resistance, stress tolerance, improved nitrogen utilization, and the like), or output traits (e.g. high oils content, healthy oil composition, nutritional improvement, and the like). Such combinations may be obtained either through conventional breeding (breeding stack) or jointly as a novel transformation event involving the simultaneous introduction of multiple genes (molecular stack). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

Target Pests

The DIG-10 toxins of the invention are particularly suitable for use in control of insects pests. Coleopterans are one important group of agricultural, horticultural, and household pests which cause a very large amount of damage each year. This insect order encompasses foliar- and root-feeding larvae and adults, including: weevils from the families Anthribidae, Bruchidae, and Curculionidae [e.g. boll weevil (*Anthonomus grandis* Boheman), rice water weevil (*Lissorhoptrus oryzophilus* Kuschel), granary weevil (*Sitophilus grananus* Linnaeus), rice weevil (*Sitophilus oryzae* Linnaeus), clover leaf weevil (*Hypera punctata* Fabricius), and maize billbug (*Sphenophorus maidis* Chittenden)]; flea beetles, cucumber beetles, rootworms, leaf beetles, potato beetles, and leaf miners in the family *Chrysomelidae* [e.g. Colorado potato beetle (*Leptinotarsa decemlineata* Say), western corn rootworm (*Diabrotica virgifera virgifera* LeConte), northern corn rootworm (*Diabrotica barben* Smith & Lawrence); southern corn rootworm (*Diabrotica undecimpunctata howardi* Barber), corn flea beetle (*Chaetocnema pulicara* Melsheimer), crucifer flea beetle (*Phyllotreta cruciferae* Goeze), grape *colaspis* (*Colaspis brunnea* Fabricius), cereal leaf beetle (*Oulema melanopus* Linnaeus), and sunflower beetle (*Zygogramma exclamationis* Fabricius)]; beetles from the family Coccinellidae [e.g. Mexican bean beetle (*Epilachna varivestis* Mulsant)]; chafers and other beetles from the family Scarabaeidae (e.g. Japanese beetle (*Popillia japonica* Newman), northern masked chafer (white grub, *Cyclocephala borealis* Arrow), southern masked chafer (white grub, *Cyclocephala immaculata* Olivier), European chafer (*Rhizotrogus majalis* Razoumowsky), white grub (*Phyllophaga crinita* Burmeister), and carrot beetle (*Ligyrus gibbosus* De Geer)]; carpet beetles from the family Dermestidae; wireworms from the family Elateridae [e.g. *Melanotus* spp., *Conoderus* spp., *Limonius* spp., *Agriotes* spp., *Ctenicera* spp., *Aeolus* spp.)]; bark beetles from the family Scolytidae, and beetles from the family Tenebrionidae (e.g. *Eleodes* spp). Any genus listed above (and others), generally, can also be targeted as a part of the subject invention. Any additional insects in any of these genera (as targets) are also included within the scope of this invention.

Lepidopterans are another important group of agricultural, horticultural, and household pests which cause a very large amount of damage each year. This insect order encompasses foliar- and root-feeding larvae and adults. Lepidopteran insect pests include, but are not limited to: *Achoroia grisella, Acleris gloverana, Acleris variana, Adoxophyes orana, Agrotis Ipsilon* (black cutworm), *Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella* (southwestern corn borer), *Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea* (corn earworm), *Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxagrotis albicosta* (western bean cutworm), *Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis* (European corn borer), *Paleacrita vernata, Papiapema nebris* (common stalk borer), *Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella* (diamondback moth), *Pontia protodice, Pseudaletia unipuncta* (armyworm), *Pseudoplasia includens, Sabulodes aegrotata, Schizura concinna, Sitotroga cerealella, Spilonta ocellana, Spodoptera frugiperda* (fall armyworm), *Spodoptera exigua* (beet armyworm), *Thaurnstopoea pityocampa, Ensola bisselliella, Trichoplusia hi, Udea rubigalis, Xylomyges curiails,* and *Yponomeuta padella*.

Use of DIG-10 toxins to control Coleopteran pests of crop plants is contemplated. In some embodiments, Cry proteins may be economically deployed for control of insect pests that include but are not limited to, for example, rootworms such as *Diabrotica undecimpunctata howardi* (southern corn rootworm), *Diabrotica longicornis barberi* (northern corn rootworm), and *Diabrotica virgifera* (western corn rootworm), and grubs such as the larvae of *Cyclocephala borealis* (northern masked chafer), *Cyclocephala immaculate* (southern masked chafer), and *Popillia japonica* (Japanese beetle).

Use of the DIG-10 toxins to control parasitic nematodes including, but not limited to, root knot nematode (*Meloidogyne icognita*) and soybean cyst nematode (*Heterodera glycines*) is also contemplated.

Antibody Detection of DIG-10 Toxins

Anti-Toxin Antibodies.

Antibodies to the toxins disclosed herein, or to equivalent toxins, or fragments of these toxins, can readily be prepared using standard procedures in this art. Such antibodies are useful to detect the presence of the DIG-10 toxins.

Once the B.t. insecticidal toxin has been isolated, antibodies specific for the toxin may be raised by conventional methods that are well known in the art. Repeated injections into a host of choice over a period of weeks or months will elicit an immune response and result in significant anti-B.t. toxin serum titers. Preferred hosts are mammalian species and more highly preferred species are rabbits, goats, sheep and mice. Blood drawn from such immunized animals may be processed by established methods to obtain antiserum (polyclonal antibodies) reactive with the B.t. insecticidal toxin. The antiserum may then be affinity purified by adsorption to the toxin according to techniques known in the art. Affinity purified antiserum may be further purified by isolating the immunoglobulin fraction within the antiserum using procedures known in the art. The resulting material will be a heterogeneous population of immunoglobulins reactive with the B.t. insecticidal toxin.

Anti-B.t. toxin antibodies may also be generated by preparing a semi-synthetic immunogen consisting of a synthetic peptide fragment of the B.t. insecticidal toxin conjugated to an immunogenic carrier. Numerous schemes and instruments useful for making peptide fragments are well known in the art. Many suitable immunogenic carriers such as bovine serum albumin or keyhole limpet hemocyanin are also well known in the art, as are techniques for coupling the immunogen and carrier proteins. Once the semi-synthetic immunogen has been constructed, the procedure for making antibodies specific for the B.t. insecticidal toxin fragment is identical to those used for making antibodies reactive with natural B.t. toxin.

Anti-B.t. toxin monoclonal antibodies (MAbs) are readily prepared using purified B.t. insecticidal toxin. Methods for producing MAbs have been practiced for over 15 years and are well known to those of ordinary skill in the art. Repeated intraperitoneal or subcutaneous injections of purified B.t. insecticidal toxin in adjuvant will elicit an immune response in most animals. Hyperimmunized B-lymphocytes are removed from the animal and fused with a suitable fusion partner cell line capable of being cultured indefinitely. Preferred animals whose B-lymphocytes may be hyperimmunized and used in the production of MAbs are mammals. More preferred animals are rats and mice and most preferred is the BALB/c mouse strain.

Numerous mammalian cell lines are suitable fusion partners for the production of hybridomas. Many such lines are available from the American Type Culture Collection (ATCC, Manassas, Va.) and commercial suppliers. Preferred fusion partner cell lines are derived from mouse myelomas and the HL-1® Friendly myeloma-653 cell line (Ventrex, Portland, Me.) is most preferred. Once fused, the resulting hybridomas are cultured in a selective growth medium for one to two weeks. Two well known selection systems are available for eliminating unfused myeloma cells, or fusions between myeloma cells, from the mixed hybridoma culture. The choice of selection system depends on the strain of mouse immunized and myeloma fusion partner used. The AAT selection system, described by Taggart and Samloff, (1983), may be used; however, the HAT (hypoxanthine, aminopterin, thymidine) selection system, described by Littlefield, (1964), is preferred because of its compatibility with the preferred mouse strain and fusion partner mentioned above. Spent growth medium is then screened for immunospecific MAb secretion. Enzyme linked immunosorbent assay (ELISA) procedures are best suited for this purpose; though, radioimmunoassays adapted for large volume screening are also acceptable. Multiple screens designed to consecutively pare down the considerable number of irrelevant or less desired cultures may be performed. Cultures that secrete MAbs reactive with the B.t. insecticidal toxin may be screened for cross-reactivity with known B.t. insecticidal toxins. MAbs that preferentially bind to the preferred B.t. insecticidal toxin may be isotyped using commercially available assays. Preferred MAbs are of the IgG class, and more highly preferred MAbs are of the $IgG_1$ and $IgG_{2a}$ subisotypes.

Hybridoma cultures that secrete the preferred MAbs may be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures preferably are re-assayed for antibody secretion and isotype to ensure that a stable preferred MAb-secreting culture has been established.

The anti-B.t. toxin antibodies are useful in various methods of detecting the claimed B.t. insecticidal toxin of the instant invention, and variants or fragments thereof. It is well known that antibodies labeled with a reporting group can be used to identify the presence of antigens in a variety of milieus. Antibodies labeled with radioisotopes have been used for decades in radioimmunoassays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the B.t. insecticidal toxin of the present invention can be bound to an immobilizing substance such as a polystyrene well or particle and used in immunoassays to determine whether the B.t. toxin is present in a test sample.

Detection Using Probes

A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization

As is well known to those skilled in molecular biology, similarity of two nucleic acids can be characterized by their tendency to hybridize. As used herein the terms "stringent conditions" or "stringent hybridization conditions" are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984):

$$T_m(° C.)=81.5° C.+16.6(\log M)+0.41(\% GC)-0.61(\% \text{formamide})-500/L;$$

where M is the molarity of monovalent cations, % GC is the percentage of guanosine and cytosine nucleotides in the DNA, % formamide is the percentage of formamide in the hybridization solution, and L is the length of the hybrid in base pairs Alternatively, the $T_m$ is described by the following formula (Beltz et al., 1983).

$$T_m(° C.)=81.5° C.+16.6(\log [Na+])+0.41(\% GC)-0.61(\% \text{formamide})-600/L$$

where [Na+] is the molarity of sodium ions, % GC is the percentage of guanosine and cytosine nucleotides in the DNA, % formamide is the percentage of formamide in the hybridization solution, and L is the length of the hybrid in base pairs Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al., 1995) Also see Sambrook et al., (1989).

Hybridization of immobilized DNA on Southern blots with radioactively labeled gene-specific probes may be performed by standard methods Sambrook et al., supra.). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology. (See, e.g. Sambrook et al., supra.) In general, hybridization and subsequent washes may be carried out under stringent conditions that allow for detection of target sequences with homology to the claimed toxin encoding genes. For double-stranded DNA gene probes, hybridization may be carried out overnight at 20-25° C. below the $T_m$ of the DNA hybrid in 6×SSPE, 5×Denhardt's Solution, 0.1% SDS, 0.1 mg/mL denatured DNA [20×SSPE is 3M NaCl, 0.2 M NaHPO$_4$, and 0.02M EDTA (ethylenediamine tetra-acetic acid sodium salt); 100×Denhardt's Solution is 20 gm/L Polyvinylpyrollidone, 20 gm/L Ficoll type 400 and 20 gm/L Bovine Serum Albumin (fraction V)].

Washes may typically be carried out as follows:
Twice at room temperature for 15 minutes in 1×SSPE, 0.1% SDS (low stringency wash).
Once at $T_m$−20° C. for 15 minutes in 0.2×SSPE, 0.1% SDS (moderate stringency wash).

For oligonucleotide probes, hybridization may be carried out overnight at 10-20° C. below the $T_m$ of the hybrid in 6×SSPE, 5×Denhardt's solution, 0.1% SDS, 0.1 mg/mL denatured DNA. $T_m$ for oligonucleotide probes may be determined by the following formula (Suggs et al., 1981).

$$T_m(°C.)=2(\text{number of T/A base pairs})+4(\text{number of G/C base pairs})$$

Washes may typically be carried out as follows:
Twice at room temperature for 15 minutes 1×SSPE, 0.1% SDS (low stringency wash).
Once at the hybridization temperature for 15 minutes in 1×SSPE, 0.1% SDS (moderate stringency wash).

Probe molecules for hybridization and hybrid molecules formed between probe and target molecules may be rendered detectable by means other than radioactive labeling. Such alternate methods are intended to be within the scope of this invention.

It should be understood that the examples and embodiments described herein are for illustrative purposes only and that various modifications or changes in light thereof will be suggested to persons skilled in the art and are to be included within the spirit and purview of this application and the scope of the appended claims Example 1

Isolation of a Gene Encoding DIG-10 Toxin

Nucleic acid encoding the insecticidal Cry protein designated herein as DIG-10 was isolated from B.t. strain PS184M1. Degenerate primers to be used as Forward and Reverse primers in PCR reactions using PS184M1 genomic DNA as template were designed based on multiple sequence alignments of each class of B.t. insecticidal toxin. The Forward Primer corresponds to bases 709 to 733 of SEQ ID NO:1, and the Reverse Primer corresponds to the complement of bases 2128 to 2141 of SEQ ID NO:1. This pair of primers was used to amplify a fragment of 1443 bp, corresponding to nucleotides 709 to 2141 of SEQ ID NO:1. This sequence was used as the anchor point to begin genome walking using methods adapted from the GenomeWalker™ Universal Kit (Clontech, Palo Alto, Calif.). The nucleic acid sequence of a fragment spanning the DIG-10 coding region was determined. SEQ ID NO:1 is the 3393 bp nucleotide sequence encoding the full length DIG-10 protein. SEQ ID NO:2 is the amino acid sequence of the full length DIG-10 protein deduced from SEQ ID NO:1.

Example 2

Deletion of Domain I α-Helices from DIG-10

To improve the insecticidal properties of the DIG-10 toxin, serial, step-wise deletions are made, each of which removes part of the N-terminus of the DIG-10 protein. The deletions remove part or all of α-helix 1 and part or all of α-helix 2 in Domain I, while maintaining the structural integrity of α-helix 3 through α-helix 7.

Deletions are designed as follows. This example utilizes the full length chimeric DNA sequence encoding the full-length DIG-10 protein e.g. SEQ ID NO:1 and SEQ ID NO:2, respectively) to illustrate the design principles with 71 specific variants. It utilizes the chimeric sequence of SEQ ID NO:5 (DNA encoding DIG-10 core toxin fused to Cry1Ab protoxin segment) to provide an additional 71 specific variants. One skilled in the art will realize that other DNA sequences encoding all or an N-terminal portion of the DIG-10 protein may be similarly manipulated to achieve the desired result. To devise the first deleted variant coding sequence, all of the bases that encode α-helix 1 including the codon for the proline residue near the beginning of α-helix 2A (i.e. P53 for the full length DIG-10 protein of SEQ ID NO:2), are removed. Thus, elimination of bases 1 through 159 of SEQ ID NO:1 removes the coding sequence for amino acids 1 through 53 of SEQ ID NO:2. Reintroduction of a translation initiating ATG (methionine) codon at the beginning (i.e. in front of the codon corresponding to amino acid 54 of the full length protein) provides for the deleted variant coding sequence comprising an open reading frame of 3237 bases which encodes a deleted variant DIG-10 protein comprising 1079 amino acids (i.e. methionine plus amino acids 54 to 1131 of the full-length DIG-10 protein). Serial, stepwise deletions that remove additional codons for a single amino acid corresponding to residues 54 through 96 of the full-length DIG-10 protein of SEQ ID NO:2 provide variants missing part or all of α-helix 2A and α-helix 2B. Thus a second designed deleted variant coding sequence requires elimination of bases 1 to 162 of SEQ ID NO:1, thereby removing the coding sequence for amino acids 1 through 54. Restoration of a functional open reading frame is again accomplished by reintroduction of a translation initiation methionine codon at the beginning of the remaining coding sequence, thus providing for a second deleted variant coding sequence having an open reading frame of 3234 bases encoding a deleted variant DIG-10 protein comprising 1078 amino acids (i.e. methionine plus amino acids 55 through 1131 of the full-length DIG-10 protein). The last designed deleted variant coding sequence requires removal of bases 1 through 288 of SEQ ID NO:1, thus eliminating the coding sequence for amino acids 1 through 96, and, after reintroduction of a translation initiation methionine codon, providing a deletion variant coding sequence having an open reading frame of 3108 bases which encodes a deletion variant DIG-10 protein of 1036 amino acids (i.e. methionine plus amino acids 97 through 1131 of the full-length DIG-10 protein). As exemplified, after elimination of the deletion sequence, an initiator methionine codon is added to the beginning of the remaining coding sequence to restore a functional open reading frame.

Also as described, an additional glycine codon is to be added between the methionine codon and the codon for the instability-determining amino acid in the instance that removal of the deleted sequence leaves exposed at the N-terminus of the remaining portion of the full-length protein one of the instability-determining amino acids as provided above.

Table 3 describes specific variants designed in accordance with the strategy described above.

TABLE 3

Deletion variant protein sequences of the full-length DIG-10 protein of SEQ ID NO: 2 and the fusion protein sequence of SEQ ID NO: 5.

| DIG-10 Deletion Variant | Residues added at NH2 terminus | Residues of SEQ ID NO: 2 | DIG-10 Deletion Variant | Residues added at NH2 terminus | Residues of SEQ ID NO: 5 |
| --- | --- | --- | --- | --- | --- |
| 1 | M | 54-1131 | 72 | M | 54-1176 |
| 2 | M | 55-1131 | 73 | M | 55-1176 |
| 3 | M | 56-1131 | 74 | M | 56-1176 |
| 4 | M | 57-1131 | 75 | M | 57-1176 |
| 5 | M | 58-1131 | 76 | M | 58-1176 |
| 6 | M | 59-1131 | 77 | M | 59-1176 |
| 7 | M | 60-1131 | 78 | M | 60-1176 |
| 8 | MG | 60-1131 | 79 | MG | 60-1176 |
| 9 | M | 61-1131 | 80 | M | 61-1176 |
| 10 | MG | 61-1131 | 81 | MG | 61-1176 |
| 11 | M | 62-1131 | 82 | M | 62-1176 |
| 12 | MG | 62-1131 | 83 | MG | 62-1176 |
| 13 | M | 63-1131 | 84 | M | 63-1176 |
| 14 | MG | 63-1131 | 85 | MG | 63-1176 |
| 15 | M | 64-1131 | 86 | M | 64-1176 |
| 16 | MG | 64-1131 | 87 | MG | 64-1176 |
| 17 | M | 65-1131 | 88 | M | 65-1176 |
| 18 | MG | 65-1131 | 89 | MG | 65-1176 |
| 19 | M | 66-1131 | 90 | M | 66-1176 |
| 20 | MG | 66-1131 | 91 | MG | 66-1176 |
| 21 | M | 67-1131 | 92 | M | 67-1176 |
| 22 | MG | 67-1131 | 93 | MG | 67-1176 |
| 23 | M | 68-1131 | 94 | M | 68-1176 |
| 24 | MG | 68-1131 | 95 | MG | 68-1176 |
| 25 | M | 69-1131 | 96 | M | 69-1176 |
| 26 | MG | 69-1131 | 97 | MG | 69-1176 |
| 27 | M | 70-1131 | 98 | M | 70-1176 |
| 28 | MG | 70-1131 | 99 | MG | 70-1176 |
| 29 | M | 71-1131 | 100 | M | 71-1176 |
| 30 | MG | 71-1131 | 101 | MG | 71-1176 |
| 31 | M | 72-1131 | 102 | M | 72-1176 |
| 32 | MG | 72-1131 | 103 | MG | 72-1176 |
| 33 | M | 73-1131 | 104 | M | 73-1176 |
| 34 | MG | 73-1131 | 105 | MG | 73-1176 |
| 35 | M | 74-1131 | 106 | M | 74-1176 |
| 36 | M | 75-1131 | 107 | M | 75-1176 |
| 37 | MG | 75-1131 | 108 | MG | 75-1176 |
| 38 | M | 76-1131 | 109 | M | 76-1176 |
| 39 | M | 77-1131 | 110 | M | 77-1176 |
| 40 | M | 78-1131 | 111 | M | 78-1176 |
| 41 | MG | 78-1131 | 112 | MG | 78-1176 |
| 42 | M | 79-1131 | 113 | M | 79-1176 |
| 43 | M | 80-1131 | 114 | M | 80-1176 |
| 44 | M | 81-1131 | 115 | M | 81-1176 |
| 45 | MG | 81-1131 | 116 | MG | 81-1176 |
| 46 | M | 82-1131 | 117 | M | 82-1176 |
| 47 | M | 83-1131 | 118 | M | 83-1176 |
| 48 | M | 84-1131 | 119 | M | 84-1176 |
| 49 | MG | 84-1131 | 120 | MG | 84-1176 |
| 50 | M | 85-1131 | 121 | M | 85-1176 |
| 51 | M | 86-1131 | 122 | M | 86-1176 |
| 52 | M | 87-1131 | 123 | M | 87-1176 |
| 53 | MG | 87-1131 | 124 | MG | 87-1176 |
| 54 | M | 88-1131 | 125 | M | 88-1176 |
| 55 | MG | 88-1131 | 126 | MG | 88-1176 |
| 56 | M | 89-1131 | 127 | M | 89-1176 |
| 57 | MG | 89-1131 | 128 | MG | 89-1176 |
| 58 | M | 90-1131 | 129 | M | 90-1176 |
| 59 | MG | 90-1131 | 130 | MG | 90-1176 |
| 60 | M | 91-1131 | 131 | M | 91-1176 |
| 61 | MG | 91-1131 | 132 | MG | 91-1176 |

TABLE 3-continued

Deletion variant protein sequences of the full-length DIG-10 protein of SEQ ID
NO: 2 and the fusion protein sequence of SEQ ID NO: 5.

| DIG-10 Deletion Variant | Residues added at NH2 terminus | Residues of SEQ ID NO: 2 | DIG-10 Deletion Variant | Residues added at NH2 terminus | Residues of SEQ ID NO: 5 |
|---|---|---|---|---|---|
| 62 | M | 92-1131 | 133 | M | 92-1176 |
| 63 | M | 93-1131 | 134 | M | 93-1176 |
| 64 | MG | 93-1131 | 135 | MG | 93-1176 |
| 65 | M | 94-1131 | 136 | M | 94-1176 |
| 66 | M | 95-1356 | 137 | M | 95-1176 |
| 67 | MG | 95-1131 | 138 | MG | 95-1176 |
| 68 | M | 96-1131 | 139 | M | 96-1176 |
| 69 | MG | 96-1131 | 140 | MG | 96-1176 |
| 70 | M | 97-1131 | 141 | M | 97-1176 |
| 71 | MG | 97-1131 | 142 | MG | 97-1176 |

Nucleic acids encoding the toxins described in Table 3 are designed in accordance with the general principles for synthetic genes intended for expression in plants, as discussed above.

Example 3

Design of a Plant-Optimized Version of the Coding Sequence for the DIG-10 B.t. Insecticidal Protein A DNA sequence having a plant codon bias was designed and synthesized to produce the DIG-5 protein in transgenic monocot and dicot plants. A codon usage table for maize (Zea mays L.) was calculated from 706 protein coding sequences (CDs) obtained from sequences deposited in GenBank. Codon usage tables for tobacco (Nicotiana tabacum, 1268 CDs), canola (Brassica napus, 530 CDs), cotton (Gossypium hirsutum, 197 CDs), and soybean (Glycine max; ca. 1000 CDs) were downloaded from data at the website kazusa.or.jp/codon/. A biased codon set that comprises highly used codons common to both maize and dicot datasets, in appropriate weighted average relative amounts, was calculated after omitting any redundant codon used less than about 10% of total codon uses for that amino acid in either plant type. To derive a plant optimized sequence encoding the DIG-5 protein, codon substitutions to the experimentally determined DIG-5 DNA sequence were made such that the resulting DNA sequence had the overall codon composition of the plant-optimized codon bias table. Further refinements of the sequence were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1). These changes were all made within the constraints of retaining the plant-biased codon composition. Synthesis of the designed sequence was performed by a commercial vendor (DNA2.0, Menlo Park, Calif.).

Additional guidance regarding the production of synthetic genes can be found in, for example, WO 97/13402 and U.S. Pat. No. 5,380,831.

A maize-optimized DNA sequence encoding the DIG-10 core toxin is given in SEQ ID NO:3. A dicot-optimized DNA sequence encoding the Cry1Ab protoxin segment is disclosed as SEQ ID NO:6. A maize-optimized DNA sequence encoding the Cry1Ab protoxin segment is disclosed as SEQ ID NO:7.

Example 4

Construction of Expression Plasmids Encoding DIG-10 Insecticidal Toxin and Expression in Bacterial Hosts Standard cloning methods are used in the construction of Pseudomonas fluorescens (Pf) expression plasmids engineered to produce full-length DIG-10 proteins encoded by plant-optimized coding regions. Restriction endonucleases are obtained from New England BioLabs (NEB; Ipswich, Mass.) and T4 DNA Ligase (Invitrogen) is used for DNA ligation. Plasmid preparations are performed using the NucleoBond® Xtra Kit (Macherey-Nagel Inc, Bethlehem, Pa.) or the Plasmid Midi Kit (Qiagen), following the instructions of the suppliers. DNA fragments are purified using the Millipore Ultrafree®-DA cartridge (Billerica, Mass.) after agarose Tris-acetate gel electrophoresis.

The basic cloning strategy entails subcloning the DIG-10 toxin coding sequence (CDS) into pDOW1169 at. for example, SpeI and XhoI restriction sites, whereby it is placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced, (US Patent Application No. 20080193974). The expression plasmid is transformed by electroporation into DC454 (a near wild-type P. fluorescens strain having mutations ΔpyrF and lsc::lacI$^{QI}$), or its derivatives, recovered in SOC-Soy hydrolysate medium, and plated on selective medium (M9 glucose agar lacking uracil, Sambrook et al., supra). Details of the microbiological manipulations are available in Squires et al., (2004), US Patent Application No. 20060008877, US Patent Application No. 20080193974, and US Patent Application No. 20080058262, incorporated herein by reference. Colonies are first screened by PCR and positive clones are then analyzed by restriction digestion of miniprep plasmid DNA. Plasmid DNA of selected clones containing inserts is sequenced, either by using Big Dye® Terminator version 3.1 as recommended by the suppler (Applied Biosystems/Invitrogen), or by contract with a commercial sequencing vendor such as MWG Biotech (Huntsville, Ala.). Sequence data is assembled and analyzed using the Sequencher™ software (Gene Codes Corp., Ann Arbor, Mich.).

Growth and Expression Analysis in Shake Flasks

Production of DIG-10 toxin for characterization and insect bioassay is accomplished by shake-flask-grown *P. fluorescens* strains harboring expression constructs (e.g. clone DP2826). Seed cultures grown in M9 medium supplemented with 1% glucose and trace elements are used to inoculate 50 mL of defined minimal medium with 5% glycerol (Teknova Cat. #3D7426, Hollister, Calif.). Expression of the DIG-10 toxin gene via the Ptac promoter is induced by addition of isopropyl-β-D-1-thiogalactopyranoside (IPTG) after an initial incubation of 24 hours at 30° C. with shaking. Cultures are sampled at the time of induction and at various times post-induction. Cell density is measured by optical density at 600 nm ($OD_{600}$). Other culture media suitable for growth of *Pseudomonas fluorescens* may also be utilized, for example, as described in Huang et al., 2007 and US Patent Application No. 20060008877.

Cell Fractionation and SDS-PAGE Analysis of Shake Flask Samples

At each sampling time, the cell density of samples is adjusted to $OD_{600}$=20 and 1 mL aliquots are centrifuged at 14000×g for five minutes. The cell pellets are frozen at −80° C. Soluble and insoluble fractions from frozen shake flask cell pellet samples are generated using EasyLyse™ Bacterial Protein Extraction Solution (EPICENTRE® Biotechnologies, Madison, Wis.). Each cell pellet is resuspended in 1 mL EasyLyse™ solution and further diluted 1:4 in lysis buffer and incubated with shaking at room temperature for 30 minutes. The lysate is centrifuged at 14,000 rpm for 20 minutes at 4° C. and the supernatant is recovered as the soluble fraction. The pellet (insoluble fraction) is then resuspended in an equal volume of phosphate buffered saline (PBS; 11.9 mM $Na_2HPO_4$, 137 mM NaCl, 2.7 mM KCl, pH7.4).

Samples are mixed 1:1 with 2× Laemmli sample buffer containing β-mercaptoethanol (Sambrook et al., supra.) and boiled for 5 minutes prior to loading onto Criterion XT Bis-Tris 12% gels (Bio-Rad Inc., Hercules, Calif.) Electrophoresis is performed in the recommended XT MOPS buffer. Gels are stained with Bio-Safe Coomassie Stain according to the manufacturer's (Bio-Rad) protocol and imaged using the Alpha Innotech Imaging system (San Leandro, Calif.).

Inclusion Body Preparation

Cry protein inclusion body (IB) preparations are performed on cells from *P. fluorescens* fermentations that produced insoluble B.t. insecticidal protein, as demonstrated by SDS-PAGE and MALDI-MS (Matrix Assisted Laser Desorption/Ionization Mass Spectrometry). *P. fluorescens* fermentation pellets are thawed in a 37° C. water bath. The cells are resuspended to 25% w/v in lysis buffer (50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (P8465 Sigma-Aldrich, St. Louis, Mo.) are added just prior to use). The cells are suspended using a hand-held homogenizer at lowest setting (Tissue Tearor, BioSpec Products, Inc., Bartlesville, Okla.). Lysozyme (25 mg of Sigma L7651, from chicken egg white) is added to the cell suspension by mixing with a metal spatula, and the suspension is incubated at room temperature for one hour. The suspension is cooled on ice for 15 minutes, then sonicated using a Branson Sonifier 250 (two 1-minute sessions, at 50% duty cycle, 30% output). Cell lysis is checked by microscopy. An additional 25 mg of lysozyme are added if necessary, and the incubation and sonication are repeated. When cell lysis is confirmed via microscopy, the lysate is centrifuged at 11,500×g for 25 minutes (4° C.) to form the IB pellet, and the supernatant is discarded. The IB pellet is resuspended with 100 mL lysis buffer, homogenized with the hand-held mixer and centrifuged as above. The IB pellet is repeatedly washed by resuspension (in 50 mL lysis buffer), homogenization, sonication, and centrifugation until the supernatant becomes colorless and the IB pellet becomes firm and off-white in color. For the final wash, the IB pellet is resuspended in sterile-filtered (0.22 μm) distilled water containing 2 mM EDTA, and centrifuged. The final pellet is resuspended in sterile-filtered distilled water containing 2 mM EDTA, and stored in 1 mL aliquots at −80° C.

SDS-PAGE analysis and quantitation of protein in IB preparations are done by thawing a 1 mL aliquot of IB pellet and diluting 1:20 with sterile-filtered distilled water. The diluted sample is then boiled with 4× reducing sample buffer [250 mM Tris, pH6.8, 40% glycerol (v/v), 0.4% Bromophenol Blue (w/v), 8% SDS (w/v) and 8% β-Mercapto-ethanol (v/v)] and loaded onto a Novex® 4-20% Tris-Glycine, 12+2 well gel (Invitrogen) run with 1× Tris/Glycine/SDS buffer (BioRad). The gel is run for approximately 60 min at 200 volts then stained with Coomassie Blue (50% G-250/50% R-250 in 45% methanol, 10% acetic acid), and destained with 7% acetic acid, 5% methanol in distilled water. Quantification of target bands is done by comparing densitometric values for the bands against Bovine Serum Albumin (BSA) samples run on the same gel to generate a standard curve.

Solubilization of Inclusion Bodies

Six mL of inclusion body suspension from Pf clone DP2826 (containing 32 mg/mL of DIG-10 protein) are centrifuged on the highest setting of an Eppendorf model 5415C microfuge (approximately 14,000×g) to pellet the inclusions. The storage buffer supernatant is removed and replaced with 25 mL of 100 mM sodium carbonate buffer, pH11, in a 50 mL conical tube. Inclusions are resuspended using a pipette and vortexed to mix thoroughly. The tube is placed on a gently rocking platform at 4° C. overnight to extract the target protein. The extract is centrifuged at 30,000×g for 30 min at 4° C., and the resulting supernatant is concentrated 5-fold using an Amicon Ultra-15 regenerated cellulose centrifugal filter device (30,000 Molecular Weight Cutoff; Millipore). The sample buffer is then changed to 10 mM CAPS [3-(cyclohexamino)1-propanesulfonic acid] pH 10, using disposable PD-10 columns (GE Healthcare, Piscataway, N.J.).

Gel Electrophoresis

The concentrated extract is prepared for electrophoresis by diluting 1:50 in NuPAGE® LDS sample buffer (Invitrogen) containing 5 mM dithiothreitol as a reducing agent and heated at 95° C. for 4 minutes. The sample is loaded in duplicate lanes of a 4-12% NuPAGE® gel alongside five BSA standards ranging from 0.2 to 2 μg/lane (for standard curve generation). Voltage is applied at 200V using MOPS SDS running buffer (Invitrogen) until the tracking dye reached the bottom of the gel. The gel is stained with 0.2% Coomassie Blue G-250 in 45% methanol, 10% acetic acid, and destained, first briefly with 45% methanol, 10% acetic acid, and then at length with 7% acetic acid, 5% methanol until the background clears. Following destaining, the gel is scanned with a Biorad Fluor-S MultiImager. The instrument's Quantity One v.4.5.2 Software is used to obtain background-subtracted volumes of the stained protein bands and to generate the BSA standard curve that is used to calculate the concentration of DIG-10 protein in the stock solution.

Example 5

Insecticidal Activity of Modified DIG-10 Protein Produced in *Pseudomonas fluorescens*

DIG-10 B.t. insecticidal toxin is tested for activity on larvae of Colepteran insects, including, for example, western corn rootworm (WCR, *Diabrotica virgifera* virgifera LeConte), southern corn rootworm (SCR, *Diabrotica undecimpunctata* howardi). DIG-10 B.t. insecticidal toxin is further tested for activity on larvae of Lepidopteran insects, including, for example, corn earworm (CEW; *Helicoverpa zea* (Boddie)), European corn borer (ECB; *Ostrinia nubilalis* (Hubner)), cry1F-resistant ECB (rECB), fall armyworm (FAW, *Spodoptera frugiperda*), Cry1F-resistant FAW (rFAW), diamondback moth (DBM; *Plutella xylostella* (Linnaeus)), cry1A-resistant DBM (rDBM), tobacco budworm (TBW; *Heliothis virescens* (Fabricius)), black cutworm (BCW; *Agrotis Ipsilon* (Hufnagel)), cabbage looper (CL; *Trichoplusia ni* (Hubner)), and beet armyworm (BAW, *Spodoptera exigua*, beet armyworm).

Sample Preparation and Bioassays

Inclusion body preparations in 10 mM CAPS pH10 are diluted appropriately in 10 mM CAPS pH 10, and all bioassays contain a control treatment consisting of this buffer, which serves as a background check for mortality or growth inhibition.

Protein concentrations in bioassay buffer are estimated by gel electrophoresis using BSA to create a standard curve for gel densitometry, which is measured using a BioRad imaging system (Fluor-S MultiImager with Quantity One software version 4.5.2). Proteins in the gel matrix are stained with Coomassie Blue-based stain and destained before reading.

Purified proteins are tested for insecticidal activity in bioassays conducted with neonateinsect larvae on artificial insect diet. Larvae of, for example, BCW, CEW, CL, DBM, rDBM, ECB, FAW and TBW are hatched from eggs obtained from a colony maintained by a commercial insectary (Benzon Research Inc., Carlisle, Pa.). WCR and SCR eggs are obtained from Crop Characteristics, Inc. (Farmington, Minn.). Larvae of rECB and rFAW are hatched from eggs harvested from proprietary colonies (Dow AgroSciences LLC, Indianapolis, Ind.).

The bioassays are conducted in 128-well plastic trays specifically designed for insect bioassays (C-D International, Pitman, N.J.). Each well contains 1.0 mL of Multi-species Lepidoptera diet (Southland Products, Lake Village, Ark.) or a proprietary diet designed for growth of Coleopteran insects (Dow AgroSciences LLC, Indianapolis, Ind.). A 40 µL aliquot of protein sample is delivered by pipette onto the 1.5 cm$^2$ diet surface of each well (26.7 µL/cm$^2$). Diet concentrations are calculated as the amount (ng) of DIG-10 protein per square centimeter (cm$^2$) of surface area in the well. The treated trays are held in a fume hood until the liquid on the diet surface has evaporated or is absorbed into the diet.

Within a few hours of eclosion, individual larvae are picked up with a moistened camel hair brush and deposited on the treated diet, one larva per well. The infested wells are then sealed with adhesive sheets of clear plastic, vented to allow gas exchange (C-D International, Pitman, N.J.). Bioassay trays are held under controlled environmental conditions (28° C., ~40% Relative Humidity, 16:8 [Light:Dark]) for 5 days, after which the total number of insects exposed to each protein sample, the number of dead insects, and the weight of surviving insects are recorded. Percent mortality and percent growth inhibition are calculated for each treatment. Growth inhibition (GI) is calculated as follows:

$$GI=[1-(TWIT/TNIT)/(TWIBC/TNIBC)]$$

where TWIT is the Total Weight of Insects in the Treatment, TNIT is the Total Number of Insects in the Treatment TWIBC is the Total Weight of Insects in the Background Check (Buffer control), and TNIBC is the Total Number of Insects in the Background Check (Buffer control).

The $GI_{50}$ is determined to be the concentration of DIG-10 protein in the diet at which the GI value is 50%. The $LC_{50}$ (50% Lethal Concentration) is recorded as the concentration of DIG-10 protein in the diet at which 50% of test insects are killed. Statistical analysis (One-way ANOVA) is done using JMP software (SAS, Cary, N.C.)

Example 6

*Agrobacterium* Transformation

Standard cloning methods are used in the construction of binary plant transformation and expression plasmids. Restriction endonucleases and T4 DNA Ligase are obtained from NEB. Plasmid preparations are performed using the NucleoSpin® Plasmid Preparation kit or the NucleoBond® AX Xtra Midi kit (both from Macherey-Nagel), following the instructions of the manufacturers. DNA fragments are purified using the QIAquick PCR Purification Kit or the QIAEX II Gel Extraction Kit (both from Qiagen) after gel isolation.

DNA fragments comprising the nucleotide sequences that encode the modified DIG-10 proteins, or fragments thereof, may be synthesized by a commercial vendor (e.g. DNA2.0, Menlo Park, Calif.) and supplied as cloned fragments in standard plasmid vectors, or may be obtained by standard molecular biology manipulation of other constructs containing appropriate nucleotide sequences. Unique restriction sites internal to each gene may be identified and a fragment of each gene synthesized, each containing a specific deletion or insertion. The modified Cry fragments may subcloned into other Cry fragments coding regions at a appropriate restriction sites to obtain a coding region encoding the desired full-length protein, fused proteins, or deleted variant proteins. For example one may identify an appropriate restriction recognition site at the start of the gene and a second internal restriction site specific for each gene, which may be used to construct variant clones.

In a non-limiting example, a basic cloning strategy may be to subclone full length or modified Cry coding sequences (CDS) into a plant expression plasmid at NcoI and SacI restriction sites. The resulting plant expression cassettes containing the appropriate Cry coding region under the control of plant expression elements, (e.g., plant expressible promoters, 3' terminal transcription termination and polyadenylate addition determinants, and the like) are subcloned into a binary vector plasmid, utilizing, for example, Gateway® technology or standard restriction enzyme fragment cloning procedures. LR Clonase™ (Invitrogen) for example, may be used to recombine the full length and modified gene plant expression cassettes into a binary plant transformation plasmid if the Gateway® technology is utilized. It is convenient to employ a binary plant transformation vector that harbors a bacterial gene that confers resistance to the antibiotic spectinomycin when the plasmid is present in *E. coli* and *Agrobacterium* cells. It is also convenient to employ a binary vector plasmid that contains a plant-expressible selectable marker gene that is functional in the desired host plants. Examples of plant-expressible selectable marker genes include but are not limited to the aminoglycoside phosphotransferase gene of transposon Tn5 (Aph II) which encodes resistance to the antibiotics kanamycin, neomycin and G418, as well as those genes which code for resistance or tolerance to glyphosate; hygromycin; methotrexate; phosphinothricin (bialaphos), imidazolinones, sulfonylureas and triazolopyrimidine herbicides, such as chlorosulfuron, bromoxynil, dalapon and the like.

Electro-competent cells of *Agrobacterium tumefaciens* strain Z707S (a streptomycin-resistant derivative of Z707; Hepburn et al., 1985) are prepared and transformed using electroporation (Weigel and Glazebrook, 2002). After electroporation, 1 mL of YEP broth (gm/L: yeast extract, 10; peptone, 10; NaCl, 5) are added to the cuvette and the cell-YEP suspension is transferred to a 15 mL culture tube for incubation at 28° C. in a water bath with constant agitation for 4 hours. The cells are plated on YEP plus agar (25 gm/L) with spectinomycin (200 µg/mL) and streptomycin (250 µg/mL) and the plates are incubated for 2-4 days at 28° C. Well separated single colonies are selected and streaked onto fresh YEP+ agar plates with spectinomycin and streptomycin as before, and incubated at 28° C. for 1-3 days.

The presence of the DIG-10 gene insert in the binary plant transformation vector is performed by PCR analysis using vector-specific primers with template plasmid DNA prepared from selected *Agrobacterium* colonies. The cell pellet from a 4 mL aliquot of a 15 mL overnight culture grown in YEP with spectinomycin and streptomycin as before is extracted using Qiagen Spin Mini Preps, performed per manufacturer's instructions. Plasmid DNA from the binary vector used in the *Agrobacterium* electroporation transformation is included as a control. The PCR reaction is completed using Taq DNA polymerase from Invitrogen per manufacture's instructions at 0.5× concentrations. PCR reactions are carried out in a MJ Research Peltier Thermal Cycler programmed with the following conditions: Step 1) 94° C. for 3 minutes; Step 2) 94° C. for 45 seconds; Step 3) 55° C. for 30 seconds; Step 4) 72° C. for 1 minute per kb of expected product length; Step 5) 29 times to Step 2; Step 6) 72° C. for 10 minutes. The reaction is maintained at 4° C. after cycling. The amplification products are analyzed by agarose gel electrophoresis (e.g. 0.7% to 1% agarose, w/v) and visualized by ethidium bromide staining. A colony is selected whose PCR product is identical to the plasmid control.

Alternatively, the plasmid structure of the binary plant transformation vector containing the DIG-10 gene insert is performed by restriction digest fingerprint mapping of plasmid DNA prepared from candidate *Agrobacterium* isolates by standard molecular biology methods well known to those skilled in the art of *Agrobacterium* manipulation.

Those skilled in the art of obtaining transformed plants via *Agrobacterium*-mediated transformation methods will understand that other *Agrobacterium* strains besides Z707S may be used to advantage, and the choice of strain may depend upon the identity of the host plant species to be transformed.

Example 7

Production of DIG-10 B.t. Insecticidal Proteins and Variants in Dicot Plants

*Arabidopsis* Transformation

*Arabidopsis thaliana* Col-01 is transformed using the floral dip method (Weigel and Glazebrook, 2002). The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: ½× Murashige and Skoog salts (Sigma-Aldrich)/Gamborg's B5 vitamins (Gold BioTechnology, St. Louis, Mo.), 10% (w/v) sucrose, 0.044 μM benzylaminopurine (10 μL/liter of 1 mg/mL stock in DMSO) and 300 μL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16-hour light/8-hour dark photoperiod. Approximately 4 weeks after dipping, the seeds are harvested.

*Arabidopsis* Growth and Selection

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Amon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron (Models CMP4030 or CMP3244; Controlled Environments Limited, Winnipeg, Manitoba, Canada) under long day conditions (16 hours light/8 hours dark) at a light intensity of 120-150 μmol/$m^2$ sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron under the above-mentioned growth conditions.

Those skilled in the art of dicot plant transformation will understand that other methods of selection of transformed plants are available when other plant expressible selectable marker genes (e.g. herbicide tolerance genes) are used.

Insect Bioassays of transgenic *Arabidopsis*

Transgenic *Arabidopsis* lines expressing modified Cry proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

Example 8

*Agrobacterium* Transformation for Generation of Superbinary Vectors

The *Agrobacterium* superbinary system is conveniently used for transformation of monocot plant hosts. Methodologies for constructing and validating superbinary vectors are well established. Standard molecular biological and microbiological methods are used to generate superbinary plasmids. Verification/validation of the structure of the superbinary plasmid is done using methodologies as described above for binary vectors.

Example 9

Production of DIG-10 B.t. Insecticidal Proteins and Variants in Monocot Plants

*Agrobacterium*-Mediated Transformation of Maize

Seeds from a High II $F_1$ cross (Armstrong et al., 1991) are planted into 5-gallon-pots containing a mixture of 95% Metro-Mix 360 soilless growing medium (Sun Gro Horticulture, Bellevue, Wash.) and 5% clay/loam soil. The plants are grown in a greenhouse using a combination of high pressure sodium and metal halide lamps with a 16:8 hour Light:Dark photoperiod. For obtaining immature $F_2$ embryos for transformation, controlled sib-pollinations are performed. Immature embryos are isolated at 8-10 days post-pollination when embryos are approximately 1.0 to 2.0 mm in size.

Infection and Co-Cultivation.

Maize ears are surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension *Agrobacterium* cells containing a superbinary vector is prepared by transferring 1-2 loops of bacteria grown on YEP solid medium containing 100 mg/L spectinomycin, 10 mg/L tetracycline, and 250 mg/L streptomycin at 28° C. for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 μM acetosyringone. The solution is vortexed until a uniform suspension is achieved, and the concentration is adjusted to a final density of 200 Klett units, using a Klett-Summerson colorimeter with a purple filter. Immature embryos are isolated directly into a micro centrifuge tube containing 2 mL of the infection medium. The medium is removed and replaced with 1 mL of the *Agrobacterium* solution with a density of 200 Klett units, and the *Agrobacterium* and embryo solution is incubated for 5 minutes at room temperature and then transferred to co-cultivation medium (LS Basal Medium, N6 vitamins, 1.5 mg/L 2,4-D, 30.0 gm/L sucrose, 6 mM L-proline, 0.85 mg/L $AgNO_3$, 100 μM acetosyringone, 3.0 gm/L Gellan gum (PhytoTechnology Laboratories, Lenexa, Kans.), pH 5.8) for 5 days at 25° C. under dark conditions.

After co-cultivation, the embryos are transferred to selective medium after which transformed isolates are obtained over the course of approximately 8 weeks. For selection of maize tissues transformed with a superbinary plasmid containing a plant expressible pat or bar selectable marker gene, an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L $AgNO_3$, 250 mg/L cefotaxime, 2.5 gm/L Gellan gum, pH 5.7) is used with Bialaphos (Gold BioTechnology). The embryos are transferred to selection media containing 3 mg/L Bialaphos until embryogenic isolates are obtained. Recovered isolates are bulked up by transferring to fresh selection medium at 2-week intervals for regeneration and further analysis.

Those skilled in the art of maize transformation will understand that other methods of selection of transformed plants are available when other plant expressible selectable marker genes (e.g. herbicide tolerance genes) are used.

Regeneration and Seed Production.

For regeneration, the cultures are transferred to "28" induction medium (MS salts and vitamins, 30 gm/L sucrose, 5 mg/L Benzylaminopurine, 0.25 mg/L 2,4-D, 3 mg/L Bialaphos, 250 mg/L cefotaxime, 2.5 gm/L Gellan gum, pH 5.7) for 1 week under low-light conditions (14 $\mu Em^{-2}s^{-1}$) then 1 week under high-light conditions (approximately 89 $\mu Em^{-2}s^{-1}$). Tissues are subsequently transferred to "36" regeneration medium (same as induction medium except lacking plant growth regulators). When plantlets grow to 3-5 cm in length, they are transferred to glass culture tubes containing SHGA medium (Schenk and Hildebrandt salts and vitamins (1972); PhytoTechnologies Labr.), 1.0 gm/L myo-inositol, 10 gm/L sucrose and 2.0 gm/L Gellan gum, pH 5.8) to allow for further growth and development of the shoot and roots. Plants are transplanted to the same soil mixture as described earlier herein and grown to flowering in the greenhouse. Controlled pollinations for seed production are conducted.

Example 10

Bioassay of Transgenic Maize

Bioactivity of the DIG-10 protein and variants produced in plant cells is demonstrated by conventional bioassay methods (see, for example Huang et al., 2006). One is able to demonstrate efficacy, for example, by feeding various plant tissues or tissue pieces derived from a plant producing a DIG-10 toxin to target insects in a controlled feeding environment. Alternatively, protein extracts may be prepared from various plant tissues derived from a plant producing the DIG-10 toxin and incorporate the extracted proteins in an artificial diet bioassay as previously described herein. It is to be understood that the results of such feeding assays are to be compared to similarly conducted bioassays that employ appropriate control tissues from host plants that do not produce the DIG-10 protein or variants, or to other control samples.

All patents, patent applications, provisional applications, and publications referred to or cited herein are incorporated by reference in their entirety to the extent they are not inconsistent with the explicit teachings of this specification. Unless specifically indicated or implied, the terms "a", "an", and "the" signify "at least one" as used herein. By the use of the term "genetic material" herein, it is meant to include all genes, nucleic acid, DNA and RNA.

For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction. The term "dsRNA" refers to double-stranded RNA.

REFERENCES

An, G., Watson, B. D., Stachel, S., Gordon, M. P., Nester, E. W. (1985) New cloning vehicles for transformation of higher plants. EMBO J. 4:277-284.

Altschul, S. F., Gish, W., Miller, W., Myers, E. W., Lipman, D. J. (1990) Basic local alignment search tool. J. Mol. Biol. 215:403-410.

Altschul, S. F., Madden, T. L., Schäffer, A. A., Zhang, J., Zhang, Z., Miller, W., Lipman, D. J. (1997) Gapped BLAST and PSI-BLAST: a new generation of protein database search programs. Nucl. Acids Res. 25:3389-3402.

Armstrong, C. L., Green, C. E., Phillips, R. L. (1991) Development and availability of germplasm with high TypeII culture formation response. Maize Genet. Coop. Newslett. 65:92-93.

Aronson, A. I., Han, E.-S., McGaughey, W., Johnson, D. (1991) The solubility of inclusion proteins from *Bacillus thuringiensis* is dependent upon protoxin composition and is a factor in toxicity to insects. Appl. Environ. Microbiol. 57:981-986.

Aronson, A. I., Geng, C., Wu. L. (1999) Aggregation of *Bacillus thuringiensis* Cry1A toxins upon binding to target insect larval midgut vesicles. Appl. Environ. Microbiol. 65:2503-2507.

Arvidson, H., Dunn, P. E., Strand, S., Aronson, A. I. (1989) Specificity of *Bacillis thuringiensis* for lepidopteran larvae: factors involved in vivo and in the structure of a purified toxin. Molec. Microbiol. 3:1533-1543.

Ausubel et al., eds. (1995) *Current Protocols in Molecular Biology*, Chapter 2 (Greene Publishing and Wiley-Interscience, New York).

Bailey, J. M., Shenov, N. R., Ronk, M., and Shively, J. E., (1992) Automated carboxy-terminal sequence analysis of peptides. Protein Sci. 1:68-80.

Beltz, G. A., Jacobs, K. A., Eickbush, T. H., Cherbas, P. T., Kafatos, F. C. (1983) Isolation of multigene families and determination of homologies by filter hybridization methods. In Wu, R., Grossman, L., Moldave, K. (eds.) Methods of Enzymology, Vol. 100 Academic Press, New York pp. 266-285.

Bown, D. P., Wilkinson, H. S., Jongsma, M. A., Gatehouse, J. A. (2004) Characterisation of cysteine proteinases responsible for digestive proteolysis in guts of larval western corn rootworm (*Diabrotica virgifera*) by expression in the yeast *Pichia pastoris*. Insect Biochem. Molec. Biol. 34:305-320.

Bravo, A., Gill, S. S., Soberon, M. (2007) Mode of action of *Bacillus thuringiensis* Cry and Cyt toxins and their potential for insect control. Toxicon 49:423-435.

Caruthers, M. H., Kierzek, R., Tang, J. Y. (1987) Synthesis of oligonucleotides using the phosphoramidite method. Bioactive Molecules (Biophosphates Their Analogues) 3:3-21.

Christeller, J. T., Laing, W. A., Markwick, N. P., Burgess, E. P. J. (1992) Midgut protease activities in 12 phytophagous lepidopteran larvae: dietary and protease inhibitor interactions. Insect Biochem. Molec. Biol. 22:735-746.

Chu, C. C., Wand, C. C., Sun, C. S., Hsu, C., Yin, K. C., Chu, C. Y., Bi, F. Y. (1975) Establishment of an efficient medium for anther culture of rice through comparative experiments on the nitrogen sources. Scientia Sinica 18:659-668.

Crameri, A., Cwirla, S., Stemmer, W. P. C. (1996a) Construction and evolution of antibody-phage libraries by DNA shuffling. Nat. Med. 2:100-103.

Crameri, A., Dawes, G., Rodriguez, E., Silver, S., Stemmer, W. P. C. (1997) Molecular evolution of an arsenate detoxification pathway by DNA shuffling. Nat. Biotech. 15:436-438.

Crameri, A., Whitehom, E. A., Tate, E., Stemmer, W. P. C. (1996b) Improved green fluorescent protein by molecular evolution using DNA shuffling. Nat. Biotech. 14:315-319.

de Maagd, R. A., Kwa, M. S., van der Klei, H., Yamamoto, T., Schipper, B., Vlak, J. M., Stiekema, W. J., Bosch, D. (1996) Domain III substitution in *Bacillus thuringiensis* delta-endotoxin Cry1A(b) results in superior toxicity for *Spodoptera exigua* and altered membrane protein recognition. Appl. Environ. Microbiol. 62:1537-1543.

de Maagd, R. A., Bravo, A., Berry, C., Crickmore, N., Schnepf, E. (2003) Structure, diversity, and evolution of protein toxins from spore-forming entomopathogenic bacteria. Annu. Rev. Genet. 37:409-433.

Diaz-Mendoza, M., Farinos, G. P., Castanera, P., Hernandez-Crespo, P., Ortego, F. (2007) Proteolytic processing of native Cry1Ab toxin by midgut extracts and purified trypsins from the Mediterranean corn borer *Sesamia nonagrioide*. J. Insect Physiol. 53:428-435.

Ellis, R. T., Stockhoff, B. A., Stamp, L., Schnepf, H. E., Schwab, G. E., Knuth, M., Russell, J., Cardineau, G. A., Narva, K. E. (2002) Novel *Bacillus thuringiensis* binary insecticidal crystal proteins active on western corn rootworm, *Diabrotica virgifera* virgifera LeConte. Appl. Environ. Microbiol. 68:1137-1145.

Englemann, F., Geraerts, W. P. M., (1980) The proteases and the protease inhibitor in the midgut of *Leucophaea maderae*. J. Insect Physiol. 261:703-710.

Fraley, R. T., Rogers, S. G., Horsch, R. B. (1986) Genetic transformation in higher plants. Crit. Rev. Plant Sci. 4:1-46.

Gazit, E., La Rocca, P., Sansom, M. S. P., Shai, Y. (1998) The structure and organization within the membrane of the helices composing the pore-forming domain of *Bacillus thuringiensis* delta-endotoxin are consistent with an "umbrella-like" structure of the pore. Proc. Nat. Acad. Sci. USA 95:12289-12294.

Ge, A., Rivers, D., Milne, R., Dean, D. H. (1991) Functional domains of *Bacillus thuringiensis* insecticidal crystal proteins. Refinement of *Heliothis virescens* and *Trichoplusia ni* specificity domains on Cry1A(c). J. Biol. Chem. 266: 17954-17958.

Gillikin, J. W., Bevilacqua, S., Graham, J. S. (1992) Partial characterization of digestive tract proteinases from western corn rootworm larvae, *Diabrotica virgifera*. Arch. Insect Biochem. Physiol. 19:285-298.

Gomez, I., Sanchez, J., Miranda, R., Bravo, A., Soberon, M. (2002) Cadherin-like receptor binding facilitates proteolytic cleavage of helix alpha-1 in domain I and oligomer pre-pore formation of *Bacillus thuringiensis* Cry1Ab toxin. FEBS Lett. 513:242-246.

Haider, M. Z., Knowles, B. H., Ellar, D. J. (1986) Specificity of *Bacillus thuringiensis* var. *colmeri* insecticidal δ-endotoxin is determined by differential proteolytic processing of the protoxin by larval gut proteases. Eur. J. Biochem. 156: 531-540.

Heckel, D. G., Gahan, L. J., Baxter, S. W., Zhao, J-Z., Shelton, A. M., Gould, F., Tabashnik, B. E. (2007) The diversity of Bt resistance genes in species of Lepidoptera. J. Invert. Pathol. 95:192-197.

Hepburn, A. G., White, J., Pearson, L., Maunders, M. J., Clarke, L. E., Prescott, A. G. Blundy, K. S. (1985) The use of pNJ5000 as an intermediate vector for the genetic manipulation of *Agrobacterium* Ti-plasmids. J. Gen. Microbiol. 131:2961-2969.

Hoagland, D. R., Amon, D. I. (1950) The water-culture method of growing plants without soil. Calif. Agr. Expt. Sta. Circ. 347.

Hofte, H., de Greve, H., Seurinck, J., Jansens, S., Mahillon, J., Ampe, C., Vandekerckhove, J., Vanderbruggen, H., van Montagu, M., Zabeau, M., Vaeck, M. (1986) "Structural and functional analysis of a cloned delta endotoxin of *Bacillus thuringiensis* berliner 1715." Eur. J. Biochem. 161:273-280.

Honée, G., Convents, D., Van Rie, J., Jansens, S., Peferoen, M., Visser, B. (1991) The C-terminal domain of the toxic fragment of a *Bacillus thuringiensis* crystal protein determines receptor binding. Mol. Microbiol. 5:2799-2806

Horton, R. M., Hunt, H. D., Ho, S. N., Pullen, J. K., Pease, L. R. (1989) Engineering hybrid genes without the use of restriction enzymes: gene splicing by overlap extension. Gene 77:61-68.

Huang, F., Rogers, L. B., Rhett, G. H. (2006) Comparative susceptibility of European corn borer, southwestern corn borer, and sugarcane borer (Lepidoptera: Crambidae) to Cry1Ab protein in a commercial *Bacillus thuringiensis* corn hybrid. J. Econ. Entomol. 99:194-202.

Huang, K-X., Badger, M., Haney, K., Evans, S. L. (2007) Large scale production of *Bacillus thuringiensis* PS149B1 insecticidal proteins Cry34Ab1 and Cry35Ab1 from *Pseudomonas fluorescens*. Prot. Express. Purific. 53:325-330.

Janmaat, A. F., Myers, A. H. (2003) Rapid evolution and the cost of resistance to *Bacillus thuringiensis* in greenhouse populations of cabbage loopers, *Trichoplusia ni*. Proc. Royal Soc. London. Ser. B, Biolog. Sci. 270:2263-2270.

Janmaat, A. F., Myers, A. H. (2005) The cost of resistance to *Bacillus thuringiensis* varies with the host plant of *Trichoplusia ni*. Proc. Royal Soc. London. Ser. B, Biolog. Sci. 272:1031-1038.

Karlin, S., Altschul, S. F. (1990) Methods for assessing the statistical significance of molecular sequence features by using general scoring schemes. Proc. Natl. Acad. Sci. USA 87:2264-2268.

Karlin, S., Altschul, S. F. (1993) Applications and statistics for multiple high-scoring segments in molecular sequences. Proc. Natl. Acad. Sci. USA 90:5873-5877.

Keller, G. H., Manak, M. M. (1993) DNA Probes, Background, Applications, Procedures. Stockton Press, New York, N.Y.

Knight, J. S., Broadwell, A. H., Grant, W. N., Shoemaker, C. B. (2004) A Strategy for Shuffling Numerous *Bacillus thuringiensis* Crystal Protein Domains. J. Econ. Entomol. 97:1805-1813.

Koiwa, H., Shade, R. E., Zhu-Salzman, K., D'Urzo, M. P., Murdock, L. L., Bressan, R. A., Hasegawa, P. M. (2000) A plant defensive cystatin (soyacystatin) targets cathepsin L-like digestive cysteine proteinases (DvCALs) in the larval midgut of western corn rootworm *Diabrotica virgifera virgifera*. FEBS Letters 471:67-70.

Larson, S. M., England, J. L., Desjarlais, J. R., Pande, V. S. (2002) Thoroughly sampling sequence space: Large-scale protein design of structural ensembles. Protein Sci. 11:2804-2813.

Lee, L.-Y., Gelvin, S. B. (2008) T-DNA binary vectors and systems. Plant Physiol. 146: 325-332.

Linsmaier, E. M., Skoog, F. (1965) Organic growth factor requirements of tobacco tissue. Physiologia Plantarum 18:100-127.

Littlefield, J. W. (1964) Selection of hybrids from matings of fibroblasts in vitro and their presumed recombinants. Science 145:709-710.

Meinkoth, J., Wahl, G. (1984) Hybridization of nucleic acids immobilized on solid supports. Anal. Biochem. 138:267-284.

Metcalf, R. L. (1986) The ecology of insecticides and the chemical control of insects. pp. 251-297. In (Marcos Kogan (ed.)) Ecological theory and integrated pest management practice. John Wiley & Sons, N.Y. 362 pp.

Moellenbeck, D. J., Peters, M. L., Bing, J. W., Rouse, J. R., Higgins, L. S., Sims, L., Nevshemal, T., Marshall, L., Ellis, R. T., Bystrak, P. G., Lang, B. A., Stewart, J. L., Kouba, K., Sondag, V., Gustafson, V., Nour, K., Xu, D., Swenson, J., Zhang, J., Czapla, T., Schwab, G., Jayne, S., Stockhoff, B. A., Narva, K., Schnepf, H. E., Stelman, S. J., Poutre, C., Koziel, M., Duck, N. (2001) Insecticidal proteins from *Bacillus thuringiensis* protect corn from corn rootworms. Nat. Biotech. 19:668-672.

Myers, E., Miller, W. (1988) Optimal alignments in linear space. CABIOS 4:11-17.

Naimov, S., Weemen-Hendriks, M., Dukiandjiev, S., de Maagd, R. A. (2001) *Bacillus thuringiensis* delta-endotoxin Cry1 hybrid proteins with increased activity against the Colorado Potato Beetle. Appl. Environ. Microbiol. 11:5328-5330.

Needleman, S. B., Wunsch, C. D. (1970) A general method applicable to the search for similarities in the amino acid sequence of two proteins. J. Mol. Biol. 48:443-453.

Nunez-Valdez, M.-E., Sanchez, J., Lina, L., Guereca, L., Bravo, A. (2001) Structural and functional studies of alpha-helix 5 region from *Bacillus thuringiensis* Cry1Ab delta-endotoxin. Biochim. Biophys. Acta, Prot. Struc. Molec. Enzymol. 1546:122-131.

Ochoa-Campuzano, C., Real, M. D., Martinez-Ramirez, A. C., Bravo, A., Rausell, C. (2007) An ADAM metalloprotease is a Cry3Aa *Bacillus thuringiensis* toxin receptor. Biochem. Biophys. Res. Commun. 362:437-442.

Pigott, C. R., Ellar, D. J. (2007) Role of receptors in *Bacillus thuringiensis* crystal toxin activity. Microbiol. Molec. Biol. Rev. 71:255-281.

Rang, C., Vachon, V., de Maagd, R. A., Villalon, M., Schwartz, J.-L., Bosch, D., Frutos, R., Laprade R. (1999) Interaction between functional domains of *Bacillus thuringiensis* insecticidal crystal proteins. Appl. Environ. Microbiol. 65:2918-2925.

Sambrook, J., Fritsch, E. F., Maniatis, T. (1989) *Molecular Cloning: A Laboratory Manual* (2nd ed., Cold Spring Harbor Laboratory Press, Plainview, N.Y.)

Schenk, R. U., Hildebrandt, A. C. (1972) Medium and techniques for induction and growth of monocotyledonous and dicotyledonous plant cell cultures. Can. J. Bot. 50:199-204

Schnepf, H. E., Tomczak, K., Ortega, J. P., Whiteley, H. R. (1990) Specificity-determining regions of a Lepidopteran-specific insecticidal protein produced by *Bacillus thuringiensis*. J. Biol. Chem. 265:20923-20930.

Soberon, M., Pardo-Lopez, L., Lopez, I., Gomez, I., Tabashnik, B. E., Bravo, A. (2007) Engineering modified Bt toxins to counter insect resistance. Science 318:1640-1642.

Squires, C. H., Retallack, D. M., Chew, L. C., Ramseier, T. M., Schneider, J. C., Talbot, H. W. (2004) Heterologous protein production in *P. fluorescens*. Bioprocess Intern. 2:54-59.

Stemmer, W. P. C. (1994a) DNA shuffling by random fragmentation and reassembly: in vitro recombination for molecular evolution. Proc. Natl. Acad. Sci. USA 91:10747-10751

Stemmer, W. P. C. (1994b) Rapid evolution of a protein in vitro by DNA shuffling. Nature 370: 389-391.

Stemmer, W. P. C. (1995) Searching sequence space. Bio/Technology 13:549-553.

Stewart, L. (2007) Gene synthesis for protein production. Encyclopedia of Life Sciences. John Wiley and Sons, Ltd.

Stewart, L., Burgin, A. B., (2005) Whole gene synthesis: a gene-o-matic future. Frontiers in Drug Design and Discovery 1:297-341.

Suggs, S. V., Miyake, T., Kawashime, E. H., Johnson, M. J., Itakura, K., R. B. Wallace, R. B. (1981) ICN-UCLA Symposium. Dev. Biol. Using Purified Genes, D. D. Brown [ed.], Academic Press, New York, 23:683-69

Tabashnik, B. E., Finson, N., Groeters, F. R., Moar, W. J., Johnson, M. W., Luo, K., Adang, M. J. (1994) Reversal of resistance to *Bacillus thuringiensis* in *Plutella xylostella*. Proc. Nat. Acad. Sci. USA 91:4120-4124.

Tabashnik, B. E., Gassmann, A. J., Crowder, D. W., Carriere, T. (2008) Insect resistance to Bt crops: evidence versus theory. Nat. Biotech. 26:199-202.

Taggart, R. T., Samloff, I. M. (1983) Stable antibody-producing murine hybridomas. Science 219:1228-1230.

Thie, N. M. R., Houseman J. G. (1990) Identification of cathepsin B, D and H in the larval midgut of Colorado potato beetle, *Leptinotarsa decemlineata* say (Coleoptera: Chrysomelidae) Insect Biochem. 20:313-318.

Thompson, J. D., Higgins, D. G., Gibson, T. J. (1994) CLUSTAL W: improving the sensitivity of progressive multiple sequence alignment through sequence weighting, position-specific gap penalties and weight matrix choice. Nucl. Acids Res. 22:4673-4680.

Tijssen, P. (1993) Laboratory Techniques in Biochemistry and Molecular Biology Hybridization with Nucleic Acid Probes, Part I, Chapter 2. P. C. van der Vliet [ed.], (Elsevier, N.Y.)

Varshaysky, A. (1997) The N-end rule pathway of protein degradation. Genes to Cells 2:13-28.

Vaughn, T., Cavato, T., Brar, G., Coombe, T., DeGooyer, T., Ford, S., Groth, M., Howe, A., Johnson, S., Kolacz, K., Pilcher, C., Prucell, J., Romano, C., English, L., Pershing, J. (2005) A method of controlling corn rootworm feeding using a *Bacillus thuringiensis* protein expressed in transgenic maize. Crop. Sci. 45:931-938.

Walters, F. S., Slatin, S. L., Kulesza, C. A., English, L. H. (1993) Ion channel activity of N-terminal fragments from Cry1A(c) delta-endotoxin. Biochem. Biophys. Res. Commun. 196:921-926.

Walters, F. S., Stacy, C. M., Lee, M. K., Palekar, N., Chen, J. S. (2008) An engineered chymotrypsin/cathepsin G site in domain I renders *Bacillus thuringiensis* Cry3A active against western corn rootworm larvae. Appl. Environ. Microbiol. 74:367-374.

Wehrmann, A., Van Vliet, A., Opsomer, C., Botterman, J., Schulz, A. (1996) The similarities of bar and pat gene products make them equally applicable for plant engineers. Nat. Biotechnol. 14:1274-1278.

Weigel, D., Glazebrook, J. [eds.] (2002) *Arabidopsis*: A Laboratory Manual. Cold Spring Harbor Press, Cold Spring Harbor, N.Y., 354 pages.

Wolfson, J. L., Murdock, L. L. (1990) Diversity in digestive proteinase activity among insects. J. Chem. Ecol. 16:1089-1102.

Worley, C. K., Ling, R., Callis, J. (1998) Engineering in vivo instability of firefly luciferase and *Escherichia coli* β-glucuronidase in higher plants using recognition elements from the ubiquitin pathway. Plant Molec. Biol. 37:337-347.

---

The invention claimed is:

1. An isolated polypeptide comprising SEQ ID NO:2 or SEQ ID NO:5, or an insecticidally active fragment thereof.

2. An isolated polynucleotide that comprises SEQ ID NO:1 or SEQ ID NO:3, wherein said polynucleotide is operably linked to a heterologous promotor.

3. An isolated polynucleotide that encodes the polypeptide of claim 1 wherein said polynucleotide is operably linked to a heterologous promoter.

* * * * *